(12) United States Patent
Fan et al.

(10) Patent No.: US 11,172,824 B2
(45) Date of Patent: Nov. 16, 2021

(54) HYBRID OCT AND SURFACE CONTOUR DENTAL IMAGING

(71) Applicant: Carestream Dental Technology Topco Limited, London (GB)

(72) Inventors: Chuanmao Fan, Rochester, NY (US); Victor C. Wong, Pittsford, NY (US)

(*) Notice: Subject to any disclaimer, the term of this patent is extended or adjusted under 35 U.S.C. 154(b) by 32 days.

(21) Appl. No.: 16/092,065

(22) PCT Filed: May 16, 2016

(86) PCT No.: PCT/US2016/032661
§ 371 (c)(1),
(2) Date: Oct. 8, 2018

(87) PCT Pub. No.: WO2017/176301
PCT Pub. Date: Oct. 12, 2017

(65) Prior Publication Data
US 2019/0117075 A1   Apr. 25, 2019

Related U.S. Application Data

(63) Continuation of application No. PCT/US2016/032661, filed on May 16, 2016.
(Continued)

(51) Int. Cl.
*A61B 5/00* (2006.01)
*G06T 7/521* (2017.01)
*G06T 7/30* (2017.01)

(52) U.S. Cl.
CPC .......... *A61B 5/0066* (2013.01); *A61B 5/0035* (2013.01); *A61B 5/0073* (2013.01);
(Continued)

(58) Field of Classification Search
None
See application file for complete search history.

(56) References Cited

U.S. PATENT DOCUMENTS 6,485,413 B1 * 11/2002 Boppart ............. A61B 1/00096
356/450
6,763,259 B1 * 7/2004 Hauger ................ A61B 90/36
356/450
(Continued)

FOREIGN PATENT DOCUMENTS

EP   2 514 363 A2   10/2012
EP   2 520 221 A1   11/2012
(Continued)

OTHER PUBLICATIONS

International Search Report and Written Opinion received for PCT Application Serial No. PCT/US2016/032661 dated Dec. 6, 2016, 10 pages.
(Continued)

*Primary Examiner* — Shawn Decenzo

(57) ABSTRACT

An optical apparatus has an OCT imaging apparatus with a first light source for low coherence light of wavelengths above a threshold wavelength and a signal detector that obtains an interference signal between low coherence light from the sample and low coherence light reflected from a reference. A surface contour imaging apparatus has a second light source that emits one or more wavelengths of surface illumination below the threshold wavelength, a camera to acquire images from illumination reflected from the sample and a probe that has a raster scanner wherein the low coherence light and the surface illumination share the same path from the raster scanner to the sample. A processor coordinates activation of the light sources, actuation of the scanner, and acquisition of data and the camera and follows instructions to display, store, or transfer images from the acquired data.

33 Claims, 24 Drawing Sheets

Related U.S. Application Data

(60) Provisional application No. 62/318,790, filed on Apr. 6, 2016.

(52) U.S. Cl.
CPC .......... *A61B 5/0077* (2013.01); *A61B 5/0088* (2013.01); *G06T 7/30* (2017.01); *G06T 7/521* (2017.01); *A61B 5/0075* (2013.01); *A61B 5/4542* (2013.01); *G06T 2207/10028* (2013.01); *G06T 2207/10101* (2013.01); *G06T 2207/20221* (2013.01)

(56) References Cited

U.S. PATENT DOCUMENTS

| | | | | |
|---|---|---|---|---|
| 7,142,312 | B2 * | 11/2006 | Quadling | G01B 11/24 356/602 |
| 7,342,668 | B2 * | 3/2008 | Quadling | G01B 11/2518 356/603 |
| 10,262,428 | B2 * | 4/2019 | Rosman | G06T 7/521 |
| 2004/0254476 | A1 * | 12/2004 | Quadling | G01B 11/25 600/476 |
| 2006/0210146 | A1 * | 9/2006 | Gu | G06K 9/2018 382/154 |
| 2008/0062429 | A1 * | 3/2008 | Liang | A61B 1/00052 356/497 |
| 2008/0063998 | A1 * | 3/2008 | Liang | A61B 5/4547 433/29 |
| 2008/0090198 | A1 * | 4/2008 | Liang | A61B 5/0066 433/29 |
| 2009/0079993 | A1 * | 3/2009 | Yatagai | G01B 11/2441 356/497 |
| 2010/0092040 | A1 * | 4/2010 | Fischer | G01B 11/25 382/106 |
| 2011/0194121 | A1 * | 8/2011 | Ertl | A61B 5/1077 356/610 |
| 2011/0292341 | A1 * | 12/2011 | Somani | A61B 3/152 351/208 |
| 2012/0013722 | A1 * | 1/2012 | Wong | G01J 3/0224 348/66 |
| 2013/0182260 | A1 * | 7/2013 | Bonnema | A61B 5/0088 356/479 |
| 2013/0330686 | A1 * | 12/2013 | Kaji | A61B 5/0066 433/30 |
| 2014/0104406 | A1 * | 4/2014 | Pfeiffer | A61C 9/0073 348/77 |
| 2014/0248576 | A1 * | 9/2014 | Tchouprakov | A61B 1/00009 433/30 |
| 2015/0029309 | A1 * | 1/2015 | Michaeli | A61B 5/0088 348/46 |
| 2015/0133778 | A1 | 5/2015 | Rivera et al. | |
| 2016/0174921 | A1 * | 6/2016 | Wikler | A61B 6/032 378/19 |
| 2018/0296080 | A1 * | 10/2018 | Glinec | A61B 1/00006 |
| 2019/0000412 | A1 * | 1/2019 | Wong | G01B 11/2504 |
| 2019/0008390 | A1 * | 1/2019 | Wong | A61B 5/0066 |
| 2019/0223729 | A1 * | 7/2019 | Frisken | A61B 3/1025 |
| 2019/0293414 | A1 * | 9/2019 | Sorimoto | G01B 11/2504 |
| 2020/0129069 | A1 * | 4/2020 | Inglese | A61B 5/0088 |

FOREIGN PATENT DOCUMENTS

| | | |
|---|---|---|
| EP | 3 439 535 A1 | 2/2019 |
| WO | 2017/176301 A1 | 10/2017 |

OTHER PUBLICATIONS

International Preliminary Report on Patentability received for PCT Application Serial No. PCT/US2016/032661 dated Oct. 18, 2018, 8 pages.

* cited by examiner

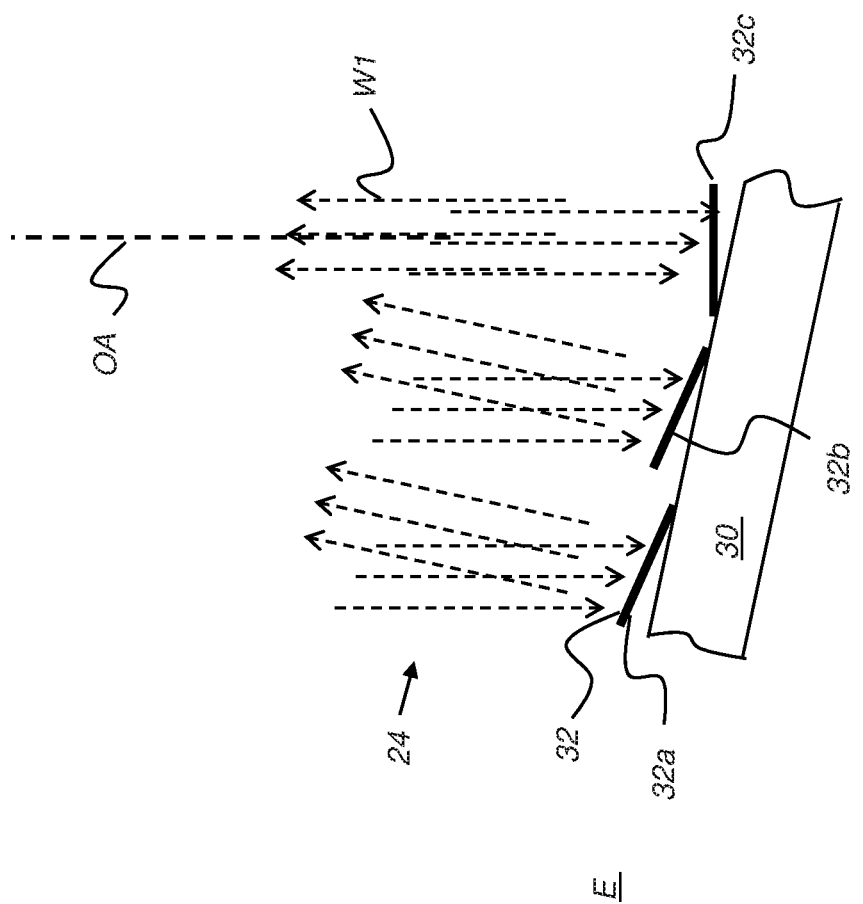

HYBRID OCT AND SURFACE CONTOUR DENTAL IMAGING

FIELD OF THE INVENTION

The disclosure relates generally to apparatus for optical coherence tomography imaging and more particularly to apparatus that combine depth imaging from optical coherence tomography with surface contour imaging capability.

BACKGROUND OF THE INVENTION

Optical coherence tomography (OCT) is a non-invasive imaging technique that employs interferometric principles to obtain high resolution, cross-sectional tomographic images that characterize the depth structure of a sample. Particularly suitable for in vivo imaging of human tissue, OCT has shown its usefulness in a range of biomedical research and medical imaging applications, such as in ophthalmology, dermatology, oncology, and other fields, as well as in ear-nose-throat (ENT) and dental imaging.

OCT has been described as a type of "optical ultrasound", imaging reflected energy from within living tissue to obtain cross-sectional data. In an OCT imaging system, light from a wide-bandwidth source, such as a super luminescent diode (SLD) or other light source, is directed along two different optical paths: a reference arm of known length and a sample arm that illuminates the tissue or other subject under study. Reflected and back-scattered light from the reference and sample arms is then recombined in the OCT apparatus and interference effects are used to determine characteristics of the surface and near-surface underlying structure of the sample. Interference data can be acquired by rapidly scanning the sample illumination across the sample. At each of several thousand points, OCT apparatus obtains an interference profile which can be used to reconstruct an A-scan with an axial depth into the material that is a factor of light source coherence. For most tissue imaging applications, OCT uses broadband illumination sources and can provide image content at depths of a few millimeters (mm).

Initial OCT apparatus employed a time-domain (TD-OCT) architecture in which depth scanning is achieved by rapidly changing the length of the reference arm using some type of mechanical mechanism, such as a piezoelectric actuator, for example. TD-OCT methods use point-by-point scanning, requiring that the illumination probe be moved or scanned from one position to the next during the imaging session. More recent OCT apparatus use a Fourier-domain architecture (FD-OCT) that discriminates reflections from different depths according to the optical frequencies of the signals they generate. FD-OCT methods simplify or eliminate axial scan requirements by collecting information from multiple depths simultaneously and offer improved acquisition rate and signal-to-noise ratio (SNR). There are two implementations of Fourier-domain OCT: spectral domain OCT (SD-OCT) and swept-source OCT (SS-OCT).

SD-OCT imaging can be accomplished by illuminating the sample with a broadband source and dispersing the reflected and scattered light with a spectrometer onto an array detector, such as a CCD (charge-coupled device) detector, for example. SS-OCT imaging illuminates the sample with a rapid wavelength-tuned laser and collects light reflected during a wavelength sweep using only a single photodetector or balanced photodetector. With both SD-OCT and SS-OCT, a profile of scattered light reflected from different depths is obtained by operating on the recorded interference signals using Fourier transforms, such as Fast-Fourier transforms (FFT), well known to those skilled in the signal analysis arts.

Because of their potential to achieve higher performance at lower cost, FD-OCT systems based on swept-frequency laser sources have attracted significant attention for medical applications that require subsurface imaging in highly scattering tissues.

One of the challenges to SS-OCT is providing a suitable light source that can generate the needed sequence of wavelengths in rapid succession. To meet this need, swept-source OCT systems conventionally employ a high-speed wavelength sweeping laser that is equipped with an intracavity monochrometer or uses some type of external cavity narrowband wavelength scanning filter for tuning laser output. Examples of external devices that have been used for this purpose include a tunable Fabry-Perot filter whose cavity length is adjusted to provide a linear change of longitudinal mode, and a polygon scanner filter that selectively reflects dispersive wavelength light. Fourier domain mode locking is a recently reported technique that has been used to generate a sweeping frequency, generally most useful for OCT imaging using broadband near infrared (BNIR) wavelengths.

References for providing a tunable laser include the following: S. R. Chinn, E. A. Swanson, and J. G. Fujimoto, "Optical coherence tomography using a frequency-tunable optical source," *Opt. Lett.* 22, 340-342 (1997).

B. Golubovic, B. E. Bouma, G. J. Tearney, and J. G. Fujimoto, "Optical frequency-domain reflectometry using rapid wavelength tuning of a Cr4+:forsterite laser," *Opt. Lett.*22, 1704-1706 (1997)

S. H. Yun, C. Boudoux, G. J. Tearney, and B. E. Bouma, "High-speed wavelength-swept semiconductor laser with a polygon-scanner-based wavelength filter," *Opt. Lett.*28, 1981-1983 (2003)

Woojin Shin, Boan-Ahn Yu, Yeung Lak Lee, Tae Jun Yu, Tae Joong Eom, Young-Chul Noh, Jongmin Lee, and Do-Kyeong Ko, "Tunable Q-switched erbium-doped fiber laser based on digital micromirror array," *Opt. Express* 14, 5356-5364 (2006), Xiao Chen, Bin-bin Yan, Fei-jun Song, Yi-quan Wang, Feng Xiao, and Kamal Alameh, "Diffraction of digital micro-mirror device gratings and its effect on properties of tunable fiber lasers," *Appl. Opt.* 51, 7214-7220 (2012).

Reference is also made to the following:

Huang, D; Swanson, E A; Lin, C P; Schuman, J S; Stinson, W G; Chang, W; Hee, M R; Flotte, T et al. (1991). "Optical coherence tomography". *Science* 254 (5035): 1178-81.

Bibcode: 1991Sci . . . 254.1178H. doi:10.1126/science.1957169.PMID 1957169;

U.S. Pat. No. 7,355,721 B2 entitled "Optical coherence tomography imaging" to Quadling et al.;

U.S. Pat. No. 8,345,261 B2 entitled "Optical coherence tomography imaging" to Quadling et al.;

U.S. Pat. Nos. 8,928,888 B2 and 8,345,257 B2, "Swept source optical coherence tomography (OCT) method and system", both to Bonnema et al.

U. S. Patent Application No. US20130330686A1 entitled "Dental optical measuring device and dental optical measuring/diagnosing tool" by Kaji et al.

For surface imaging of the teeth, various methods using light triangulation have been employed. These include structured light imaging, in which a structured pattern of light, generally of visible or near-visible infrared (NIR) wavelengths, is directed onto the tooth surface and the resulting pattern, modulated by the tooth surface, is detected by a camera. Interpretation of distortion of the projected pattern in the acquired images enables an accurate characterization of the tooth surface. The detected image information can be used, for example to form a mesh or point cloud that maps features of the tooth surface and can be used, along with other types of depth imaging, to provide useful information that can aid in dental diagnosis and treatment.

The combined results from OCT and structured light imaging can provide useful information for dental imaging. Proposed approaches for obtaining this combination in a single apparatus solution, however, have been characterized by a number of problems, including optical crosstalk between measurement types, difficulties in achieving optimal image quality in simultaneous surface and OCT measurements, workflow constraints, and computational complexity, with considerable processing overhead. Clearly, there would be advantages for improved performance and workflow using a dental imaging device that combines OCT and surface contour imaging capabilities.

SUMMARY OF THE INVENTION

An aspect of this application is to advance the art of dental imaging systems.

Another aspect of this application is to address in whole or in part, at least the foregoing and other deficiencies in the related art.

It is another aspect of this application to provide in whole or in part, at least the advantages described herein.

It is an object of the present disclosure to advance the art of diagnostic imaging and to address the need for simultaneous or near-simultaneous OCT and surface contour imaging and for registering OCT depth data to surface contour information. An embodiment of the present invention provides apparatus and methods that enable both types of imaging to be performed from a single device, configured to acquire either or both surface contour and OCT depth imaging content.

These objects are given only by way of illustrative example, and such objects may be exemplary of one or more embodiments of the invention. Other desirable objectives and advantages inherently achieved by the disclosed methods may occur or become apparent to those skilled in the art. The invention is defined by the appended claims.

According to an aspect of the present disclosure, there is provided an optical apparatus for imaging a sample, the apparatus comprising: an OCT imaging apparatus having:
a) a first light source that generates low coherence light of wavelengths above a threshold wavelength;
b) a signal detector that obtains an interference signal between a first portion of the low coherence light scattered from the sample and a second portion of the low coherence light reflected from a reference; a surface contour imaging apparatus having:
a) a second light source that emits one or more wavelengths of surface illumination below the threshold wavelength;
b) a camera disposed at an oblique angle with respect to the direction of the surface illumination incident at the sample to acquire images from the illumination reflected from the sample;
a probe that has a raster scanner wherein the low coherence light and the surface illumination share the same path from the raster scanner to the sample; and
a processor that is programmed with instructions that coordinate activation of the first and second light sources, actuation of the raster scanner, and acquisition of data from the signal detector and the camera and further programmed with instructions to display, store, or transfer images from the acquired data.

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other. Some exaggeration may be necessary in order to emphasize basic structural relationships or principles of operation. Some conventional components that would be needed for implementation of the described embodiments, such as support components used for providing power, for packaging, and for mounting and protecting system optics, for example, are not shown in the drawings in order to simplify description.

FIG. 2B is an enlarged view of a portion of the micro-mirror array of the programmable filter.

DETAILED DESCRIPTION OF THE INVENTION

Figure 1:
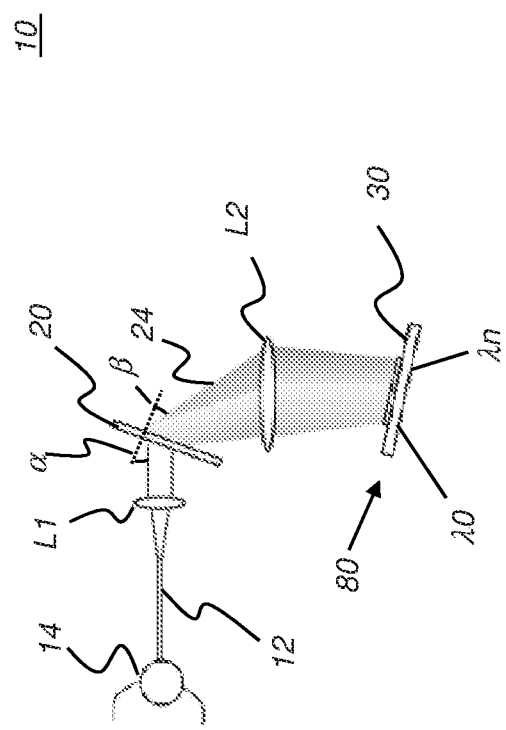
FIG. 1 is a schematic diagram that shows a programmable filter according to an embodiment of the present disclosure.

The following is a detailed description of exemplary embodiments, reference being made to the drawings in which the same reference numerals identify the same elements of structure in each of the several figures.

Where they are used in the context of the present disclosure, the terms "first", "second", and so on, do not necessarily denote any ordinal, sequential, or priority relation, but are simply used to more clearly distinguish one step, element, or set of elements from another, unless specified otherwise.

As used herein, the term "energizable" relates to a device or set of components that perform an indicated function upon receiving power and, optionally, upon receiving an enabling signal.

In the context of the present disclosure, the term "optics" is used generally to refer to lenses and other refractive, diffractive, and reflective components or apertures used for shaping and orienting a light beam. An individual component of this type is termed an optic.

In the context of the present disclosure, the term "scattered light" is used generally to include light that is reflected and backscattered from an object.

In the context of the present disclosure, the terms "viewer", "operator", and "user" are considered to be equivalent and refer to the viewing practitioner, technician, or other person who may operate a camera or scanner and may also view and manipulate an image, such as a dental image, on a display monitor. An "operator instruction" or "viewer instruction" is obtained from explicit commands entered by the viewer, such as by clicking a button on the camera or scanner or by using a computer mouse or by touch screen or keyboard entry.

In the context of the present disclosure, the phrase "in signal communication" indicates that two or more devices and/or components are capable of communicating with each other via signals that travel over some type of signal path. Signal communication may be wired or wireless. The signals may be communication, power, data, or energy signals. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

In the context of the present disclosure, the term "camera" relates to a device that is enabled to acquire a reflectance, 2-D digital image from reflected visible or NIR light, such as structured light that is reflected from the surface of teeth and supporting structures.

The general term "scanner" relates to an optical system that projects a scanned light beam of broadband near-IR (BNIR) light that is directed to the tooth surface through a sample arm and acquired, as scattered light returned in the sample arm, for detecting interference with light from a reference arm used in OCT imaging of a surface. The term "raster scanner" relates to the combination of hardware components that scan light toward a sample, as described in more detail subsequently.

The term "subject" refers to the tooth or other portion of a patient that is being imaged and, in optical terms, can be considered equivalent to the "object" of the corresponding imaging system.

In the context of the present disclosure, the phrase "broadband light emitter" refers to a light source that emits a continuous spectrum output over a range of wavelengths at any given point of time. Short-coherence or low-coherence, broadband light sources can include, for example, super luminescent diodes, short-pulse lasers, many types of white-light sources, and supercontinuum light sources. Most short coherence length sources of these types have a coherence length on the order of tens of microns or less.

In the context of the present disclosure, the term "oblique" describes an angular orientation that is not an integer multiple of 90 degrees. Two lines or light paths can be considered to be oblique with respect to each other, for example, if they diverge from or converge toward each other at an angle that is about 5 degrees or more away from parallel, or about 5 degrees or more away from orthogonal.

In the context of the present disclosure, two wavelengths can be considered to be "near" each other when within no more than +/−10 nm apart.

According to an embodiment of the present disclosure, there is provided a programmable light source that can provide variable wavelength illumination. The programmable light source can be used as a swept-source for scanned SS-OCT and other applications that benefit from a controllably changeable spectral pattern.

Referring to FIG. 1, there is shown a programmable filter 10 that is used for generating a desired pattern and sequence of wavelengths (λ0 . . . λn) from a low-coherence, broadband light source. Broadband light from a fiber laser or other source is directed, through a circulator 14 through an optical fiber or other waveguide 12 to a collimator lens L1 that directs the collimated light to a light dispersion optic 20, such as a diffraction grating. Light dispersion optic 20 forms a spectrally dispersed output beam 24, directed toward a focusing lens L2. Lens L2 focuses the dispersed light onto a spatial light modulator 80, such as a micro-mirror array 30. The micro-mirror array can be a linear array of reflective devices or a linear portion of a Digital Light Processor (DLP) from Texas Instruments, Dallas, Tex. One or more individual reflectors in array 30 is actuated to reflect light of corresponding wavelengths back through the optical path. This reflected light is the output of programmable filter 10 and can be used in applications such as optical coherence tomography (OCT) as described subsequently. Rapid actuation of each successive reflector in array 30 allows sampling of numerous small spectral portions of a spectrally dispersed output beam, such as that provided in FIG. 1. For example, where the spatial light modulator 80 is a micro-mirror array 30 that has 2048 micro-mirror elements in a single row, where the spectral range from one side of the array 30 to the other is 35 nm, each individual micro-mirror can reflect a wavelength band that is approximately 0.017 nm wide. One typical swept source sequence advances from lower to higher wavelengths by actuating a single spatial light modulator 80 pixel (reflective element) at a time, along the line formed by the spectrally dispersed output beam. Other swept source sequences are possible, as described subsequently.

Figure 2A:
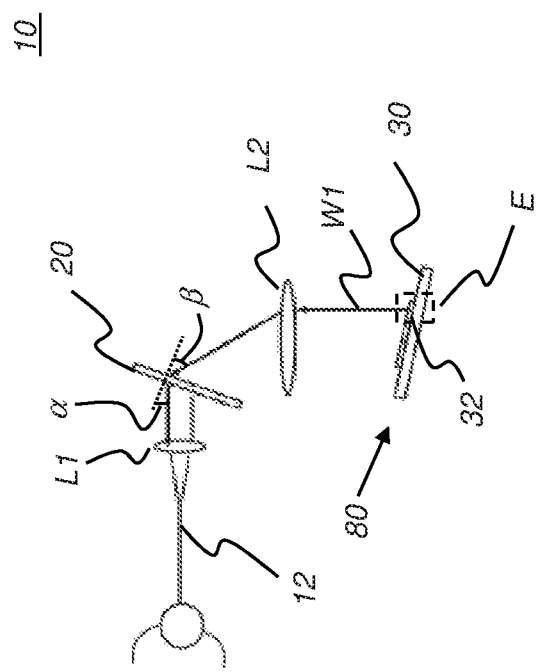
FIG. 2A is a simplified schematic diagram that shows how the programmable filter provides light of a selected wavelength band.
Figure 3:
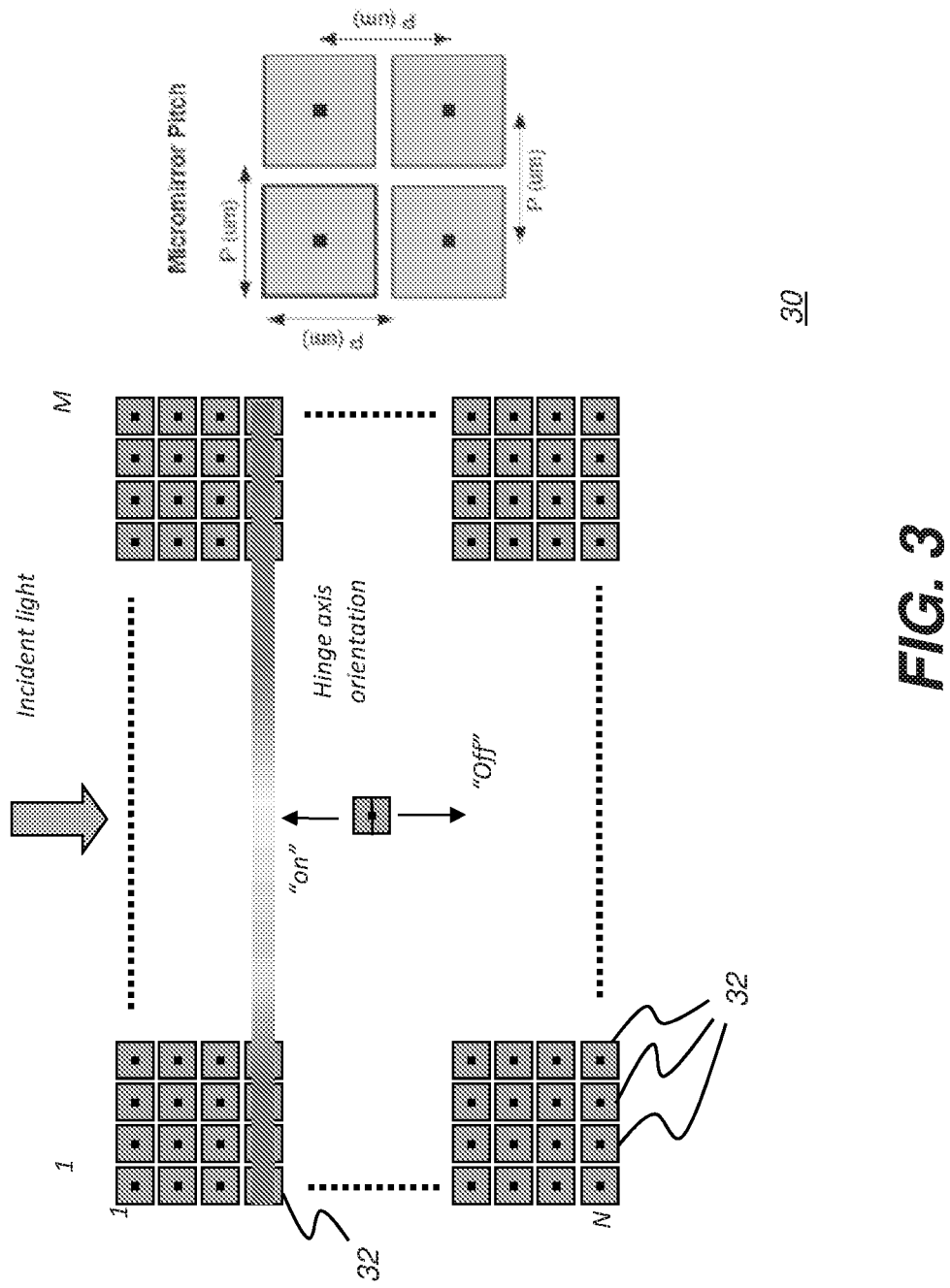
FIG. 3 is a plan view that shows the arrangement of micro-mirrors in the array.

The micro-mirror array 30 described herein and shown in FIGS. 1-3 and following is one type of possible spatial light modulator 80 that can be used as part of a programmable light source. The spatial light modulator 80 that is employed is a reflective device of some type, with discretely addressable elements that effectively provide the "pixels" of the device.

Programmable filter 10 resembles aspects of a spectrometer in its overall arrangement of components and in its light distribution. Incident broadband BNIR light is dispersed by light dispersion optic 20 in order to spatially separate the spectral components of the light. The micro-mirror array 30 or other type of spatial light modulator 80, as described in more detail subsequently, is disposed to reflect a selected wavelength band or bands of this light back through programmable filter 10 so that the selected wavelength band can be used elsewhere in the optical system, such as for use in an interferometry measurement device or for tuning a laser.

The simplified schematic of FIG. 2A and enlargement of FIG. 2B show how programmable filter 10 operates to provide light of a selected wavelength band W1. FIG. 2B, which schematically shows a greatly enlarged area E of micro-mirror array 30, shows the behavior of three mirrors 32a, 32b, and 32c with respect to incident light of beam 24. Each mirror 32 element of micro-mirror array 30 can have either of two states: deactuated, tilted at one angle, as shown at mirrors 32a and 32b; or actuated, tilted at an alternate angle as shown at mirror 32c. For DLP devices, the tilt angles for deactuated/actuated states of the micro-mirrors are +12 and −12 degrees from the substrate surface. Thus, in order to direct light back along optical axis OA through lens L2 and through the other components of programmable filter 10, micro-mirror array 30 is itself tilted at +12 degrees relative to the optical axis OA, as shown in FIG. 2B.

In the programmable filter 10 of FIG. 1, light dispersion optic 20 can be a diffraction grating of some type, including a holographic diffraction grating, for example. The grating dispersion equation is:

$$m\lambda = d(\sin \alpha + \sin \beta) \quad \text{(eq. 1)}$$

wherein:
$\lambda$ is the optical wavelength;
d is the grating pitch;
$\alpha$ is the incident angle (see FIGS. 1, 2A), relative to a normal to the incident surface of optic 20;
$\beta$ is the angle of diffracted light, relative to a normal to the exit surface of optic 20;
m is the diffraction order, generally m=1 with relation to embodiments of the present disclosure.

The FWHM (full-width half-maximum) bandwidth is determined by the spectral resolution of the grating $\delta\lambda_g$ and wavelength range on a pixel or micro-mirror 32 of the DLP device $\delta\lambda_{DLP}$, which are given as:

$$\delta\lambda_g = \lambda c \, d \cos \alpha / D \quad \text{(eq. 2)}$$

and $$\delta\lambda_{DLP} = dp \cos \beta / f \quad \text{(eq. 3)}$$

wherein:
D is the $1/e^2$ width of the incident Gaussian beam collimated by lens L1;
$\lambda c$ is the central wavelength;
d is the grating pitch;
p is the DLP pixel pitch, for each micro-mirror;
f is the focus length of focus lens L2.

The final FWHM bandwidth $\delta\lambda$ is the maximum of ($\delta\lambda_g$, $\delta\lambda_{DLP}$). Bandwidth $\delta\lambda$ defines the finest tunable wavelength range. For a suitable configuration for OCT imaging, the following relationship holds:

$$\delta\lambda_g \leq \delta\lambda_{DLP}.$$

In order to use the DLP to reflect the light back to the waveguide 12 fiber, the spectrally dispersed spectrum is focused on the DLP surface, aligned with the hinge axis of each micro-mirror 32. The DLP reference flat surface also tilts 12 degrees so that when a particular micro-mirror 32 is in an "on" state, the light is directly reflected back to the optical waveguide 12. When the micro-mirror is in an "on" state, the corresponding focused portion of the spectrum, with bandwidth corresponding to the spatial distribution of light incident on that micro-mirror, is reflected back to the waveguide 12 fiber along the same path of incident light, but traveling in the opposite direction. Circulator 14 in the fiber path guides the light of the selected spectrum to a third fiber as output. It can be readily appreciated that other types of spatial light modulator 80 may not require orientation at an oblique angle relative to the incident light beam, as was shown in the example of FIG. 2B.

The $1/e^2$ Gaussian beam intensity diameter focused on a single DLP pixel is as follows:

$$w = 4\lambda f / (\pi D \cos \beta / \cos \alpha) \quad \text{(eq. 4)}$$

Preferably, the following holds: w≤p. This sets the beam diameter w at less than the pixel pitch p. The maximum tuning range is determined by:

$$M \times \delta\lambda_{DLP},$$

wherein M is the number of DLP micro-mirrors in the horizontal direction, as represented in FIG. 3. As FIG. 3 shows, the array of micro-mirrors for micro-mirror array 30 has M columns and N rows. Only a single row of the DLP micro-mirror array is needed for use with programmable filter 10; the other rows above and below this single row may or may not be used.

The wavelength in terms of DLP pixels (micro-mirrors) can be described by the following grating equation:

$$\lambda_i = d\left(\sin \alpha + \sin\left(\tan^{-1}\left[\frac{p}{f}\left(\frac{N}{2} - i - 1\right)\right] + \beta\right)\right) \quad \text{(eq. 5)}$$

Wherein i is an index for the DLP column, corresponding to the particular wavelength, in the range between 0 and (M−1).

From the above equation (5), the center wavelength corresponding to each mirror in the row can be determined.

Figure 4:
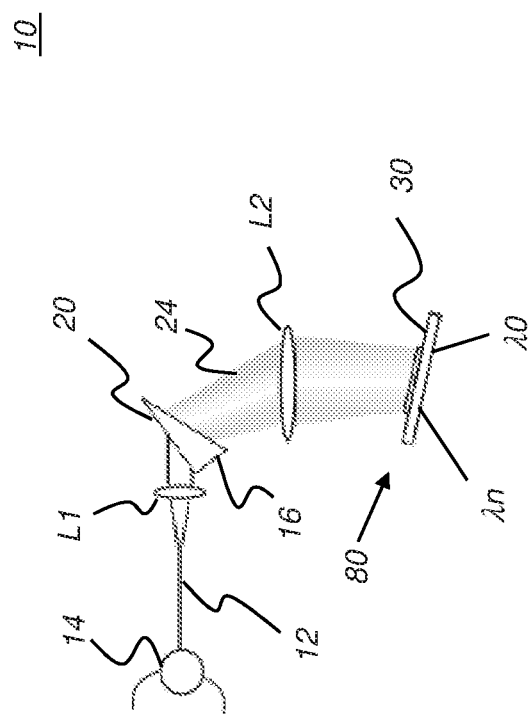
FIG. 4 is a schematic diagram that shows a programmable filter using a prism as its dispersion optic, according to an alternate embodiment of the present disclosure.

FIG. 4 shows programmable filter 10 in an alternate embodiment, with a prism 16 as light dispersion optic 20. The prism 16 disperses the light wavelengths ($\lambda n \ldots \lambda 0$) in the opposite order from the grating shown in FIG. 1. Longer wavelengths (red) are dispersed at a higher angle, shorter wavelengths (blue) at lower angles.

Figure 5:
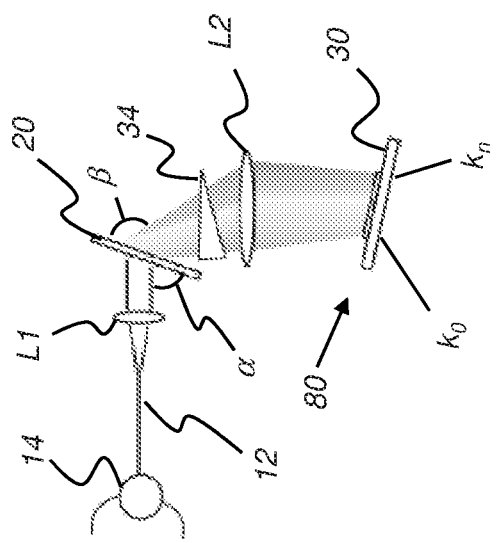
FIG. 5 is a schematic diagram showing a programmable filter that performs wavelength-to-wavenumber transformation, according to an alternate embodiment of the present disclosure.

Conventional light dispersion optics distribute the dispersed light so that its constituent wavelengths have a linear distribution. That is, the wavelengths are evenly spaced apart along the line of dispersed light. However, for Fourier domain OCT processing, conversion of wavelength data to frequency data is needed. Wavelength data ($\lambda$ in units of nm) must thus be converted to wave-number data ($k=\lambda^{-1}$), proportional to frequency. In conventional practice, an interpolation step is used to achieve this transformation, prior to Fourier transform calculations. The interpolation step requires processing resources and time. However, it would be most advantageous to be able to select wave-number k values directly from the programmable filter. The schematic diagram of FIG. 5 shows one method for optical conversion of wavelength ($\lambda_0 \ldots \lambda_N$) data to wave-number ($k_0 \ldots k_N$) data using an intermediate prism 34. Methods for specifying prism angles and materials parameters for wavelength-to-wavenumber conversion are given, for example, in an article by Hu and Rollins entitled "Fourier domain optical coherence tomography with a linear-in-wavenumber spectrometer" in *OPTICS LETTERS*, Dec. 15, 2007, vol. 32 no. 24, pp. 3525-3527.

Programmable filter 10 is capable of providing selected light wavelengths from a broadband light source in a sequence that is appropriately timed for functions such as OCT imaging using a tuned laser. Because it offers a programmable sequence, the programmable filter 10 can perform a forward spectral sweep from lower to higher wavelengths as well as a backward sweep in the opposite direction, from higher to lower wavelengths. A triangular sweep pattern, generation of a "comb" of wavelengths, or arbitrary wavelength pattern can also be provided.

For OCT imaging in particular, various programmable sweep paradigms can be useful to extract moving objects in imaging, to improve sensitivity fall-off over depth, etc. The OCT signal sensitivity decreases with increasing depth into the sample, with depth considered to extend in the z-axis direction. Employing a comb of discrete wavelengths, for example, can increase OCT sensitivity. This is described in an article by Bajraszewski et al. entitled "Improved spectral optical coherence tomography using optical frequency comb" in *Optics Express*, Vol. 16 No. 6, March 2008, pp. 4163-4176.

Figure 6A:
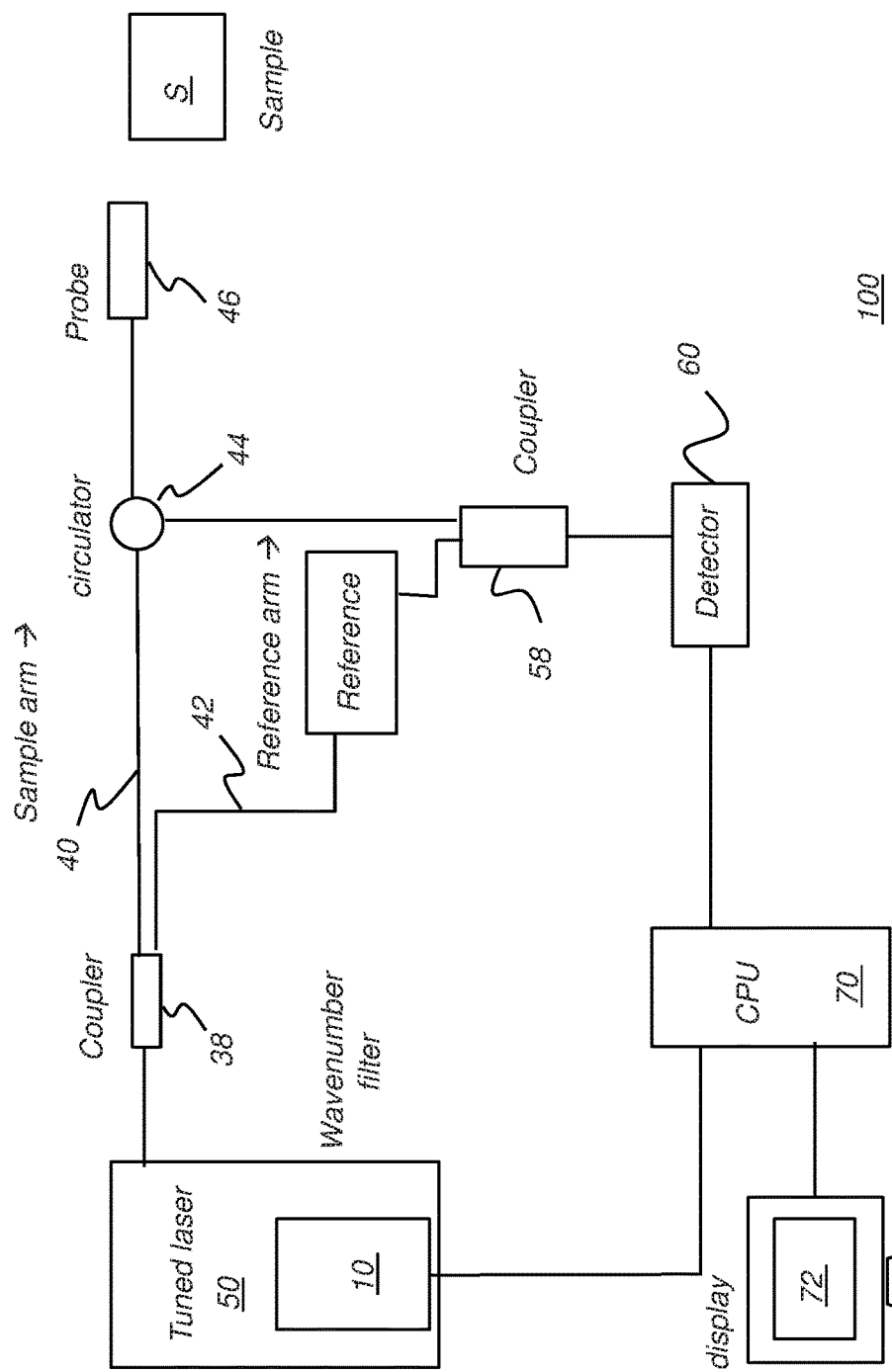
FIG. 6A is a schematic diagram showing a swept-source OCT (SS-OCT) apparatus using a programmable filter according to an embodiment of the present disclosure that uses a Mach-Zehnder interferometer.
Figure 6B:
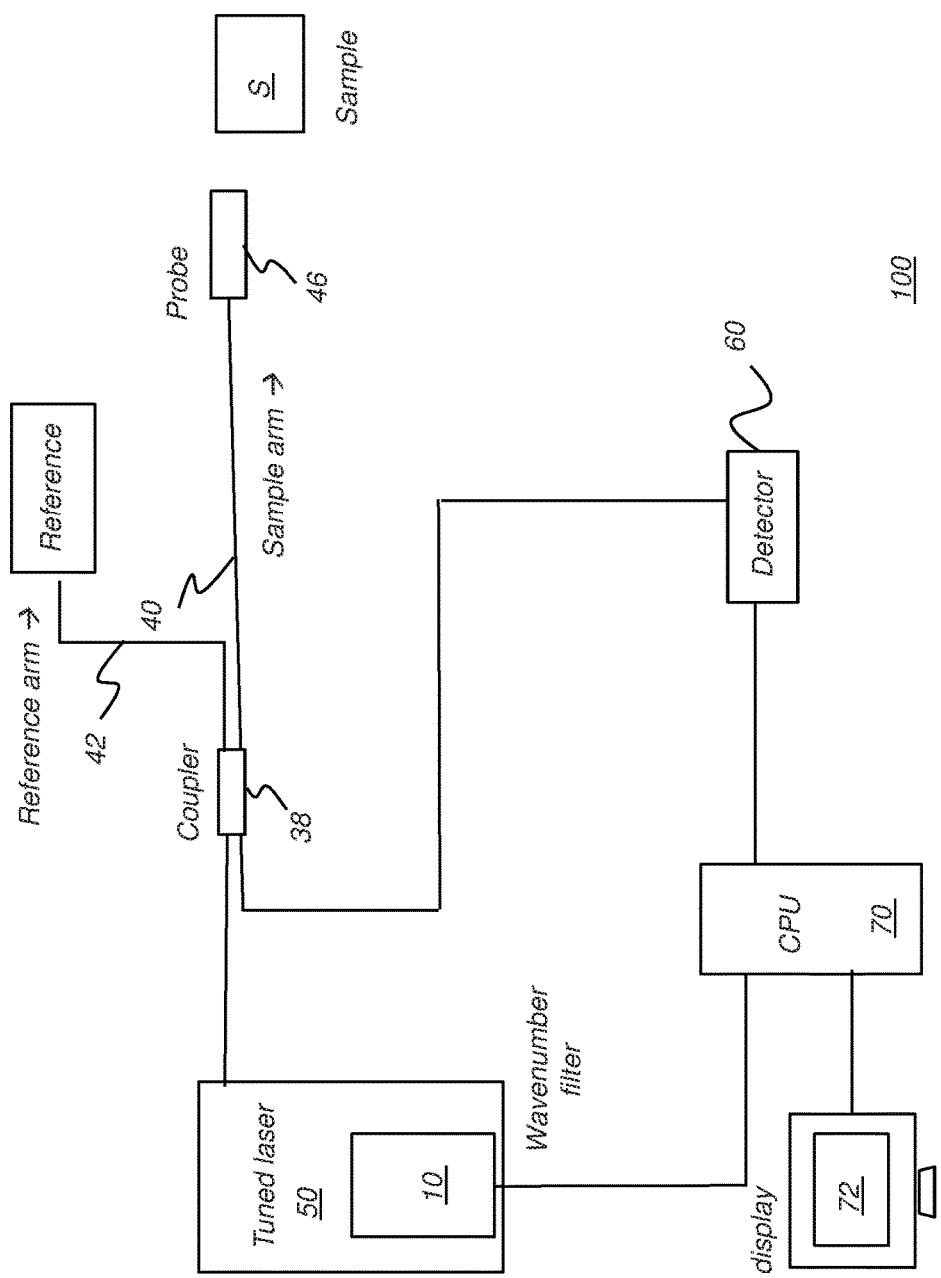
FIG. 6B is a schematic diagram showing a swept-source OCT (SS-OCT) apparatus using a programmable filter according to an embodiment of the present disclosure that uses a Michelson interferometer.

The simplified schematic diagrams of FIGS. 6A and 6B each show a swept-source OCT (SS-OCT) apparatus 100 using programmable filter 10 according to an embodiment of the present disclosure. In each case, programmable filter 10 is used as part of a tuned laser 50. For intraoral OCT, for example, laser 50 can be tunable over a range of frequencies (wave-numbers k) corresponding to wavelengths between about 400 and 1600 nm. According to an embodiment of the present disclosure, a tunable range of 35 nm bandwidth centered about 830 nm is used for intraoral OCT.

In the FIG. 6A embodiment, a Mach-Zehnder interferometer system for OCT scanning is shown. FIG. 6B shows components for a Michelson interferometer system. For these embodiments, programmable filter 10 provides part of the laser cavity to generate tuned laser 50 output. The variable laser 50 output goes through a coupler 38 and to a sample arm 40 and a reference arm 42. In FIG. 6A, the sample arm 40 signal goes through a circulator 44 and to a probe 46 for measurement of a sample S. The sampled signal is directed back through circulator 44 (FIG. 6A) and to a detector 60 through a coupler 58. In FIG. 6B, the signal goes directly to sample arm 40 and reference arm 42; the sampled signal is directed back through coupler 38 and to detector 60. The detector 60 may use a pair of balanced photodetectors configured to cancel common mode noise. A control logic processor (control processing unit CPU) 70 is in signal communication with tuned laser 50 and its programmable filter 10 and with detector 60 and obtains and processes the output from detector 60. CPU 70 is also in signal communication with a display 72 for command entry and OCT results display.

Figure 7:
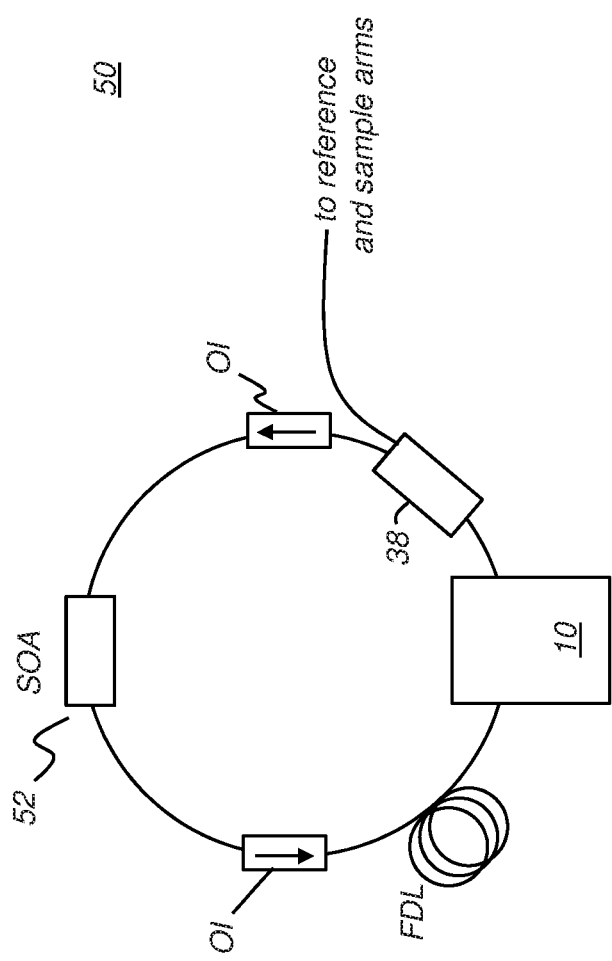
FIG. 7 is a schematic diagram that shows a tunable laser using a programmable filter according to an embodiment of the present disclosure.

The schematic diagram of FIG. 7 shows components of tuned laser 50 according to an alternate embodiment of the present disclosure. Tuned laser 50 is configured as a fiber ring laser having a broadband gain medium such as a semiconductor optical amplifier (SOA) 52. Two optical isolators OI provide protection of the SOA from back-reflected light. A fiber delay line (FDL) determines the effective sweep rate of the laser. Filter 10 has an input fiber and output fiber, used to connect the fiber ring.

Figure 8:
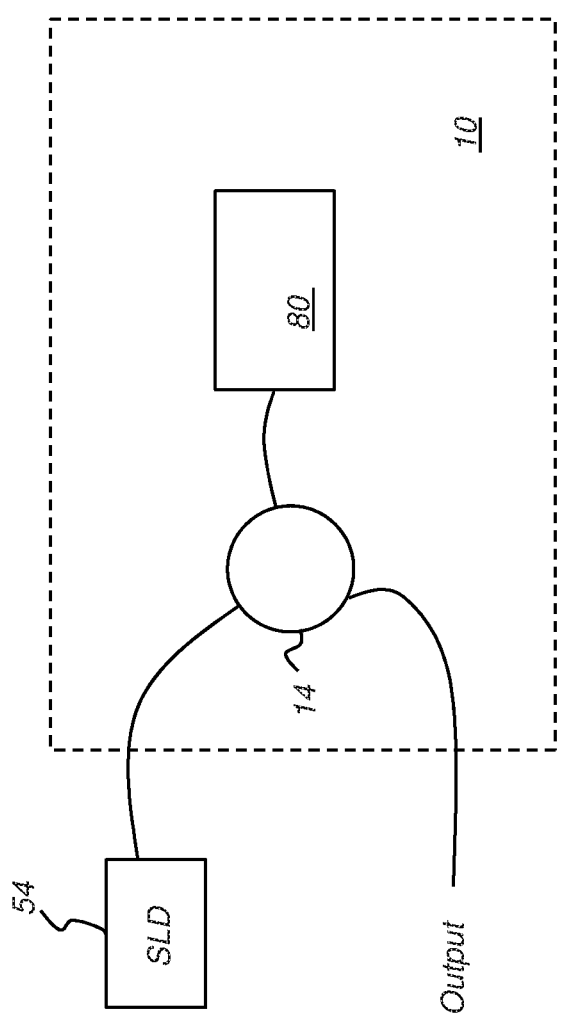
FIG. 8 is a schematic diagram that shows use of a programmable filter for selecting a wavelength band from a broadband light source.

The schematic diagram of FIG. 8 shows the use of programmable filter 10 for selecting a wavelength band from a broadband light source 54, such as a super luminescent diode (SLD). Here, spatial light modulator 80 reflects a component of the broadband light through circulator 14. Circulator 14 is used to direct light to and from the programmable filter 10 along separate optical paths.

Figure 9:
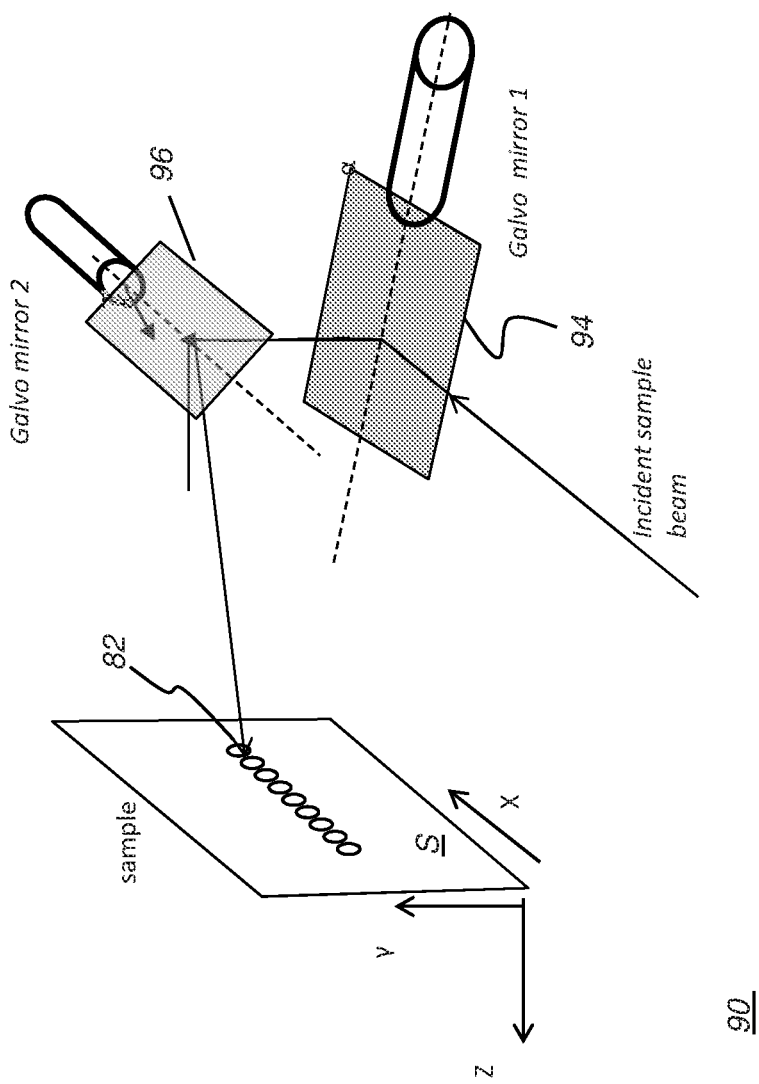
FIG. 9 shows galvo mirrors used to provide a 2-D scan as part of the OCT imaging system probe.

As shown in the schematic diagram of FIG. 9, galvo mirrors 94 and 96 cooperate to provide the raster scanning needed for OCT imaging. In the arrangement that is shown, galvo mirror 1 (94) scans the wavelengths of light to each point 82 along the sample to generate data along a row, which provides the B-scan, described in more detail subsequently. Galvo mirror 2 (96) progressively moves the row position to provide 2-D raster scanning to additional rows. At each point 82, the full spectrum of light provided using programmable filter 10, pixel by pixel of the spatial light modulator 80 (FIGS. 1, 4, 5), is rapidly generated in a single sweep and the resulting signal measured at detector 60 (FIGS. 6A, 6B).

Scanning Sequence for OCT Imaging

Figure 10A:
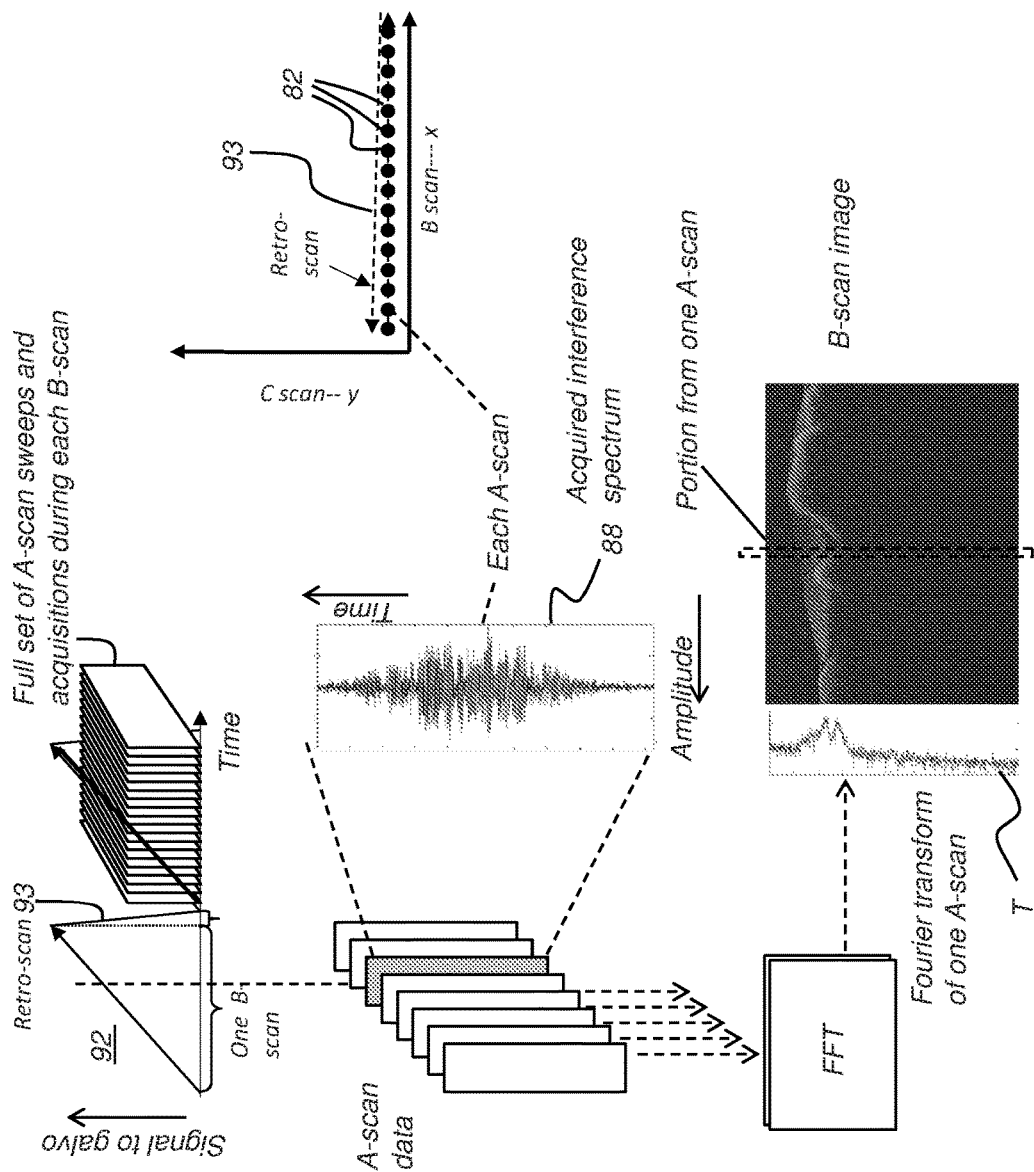
FIG. 10A shows a schematic representation of scanning operation for obtaining a B-scan.
Figure 10B:
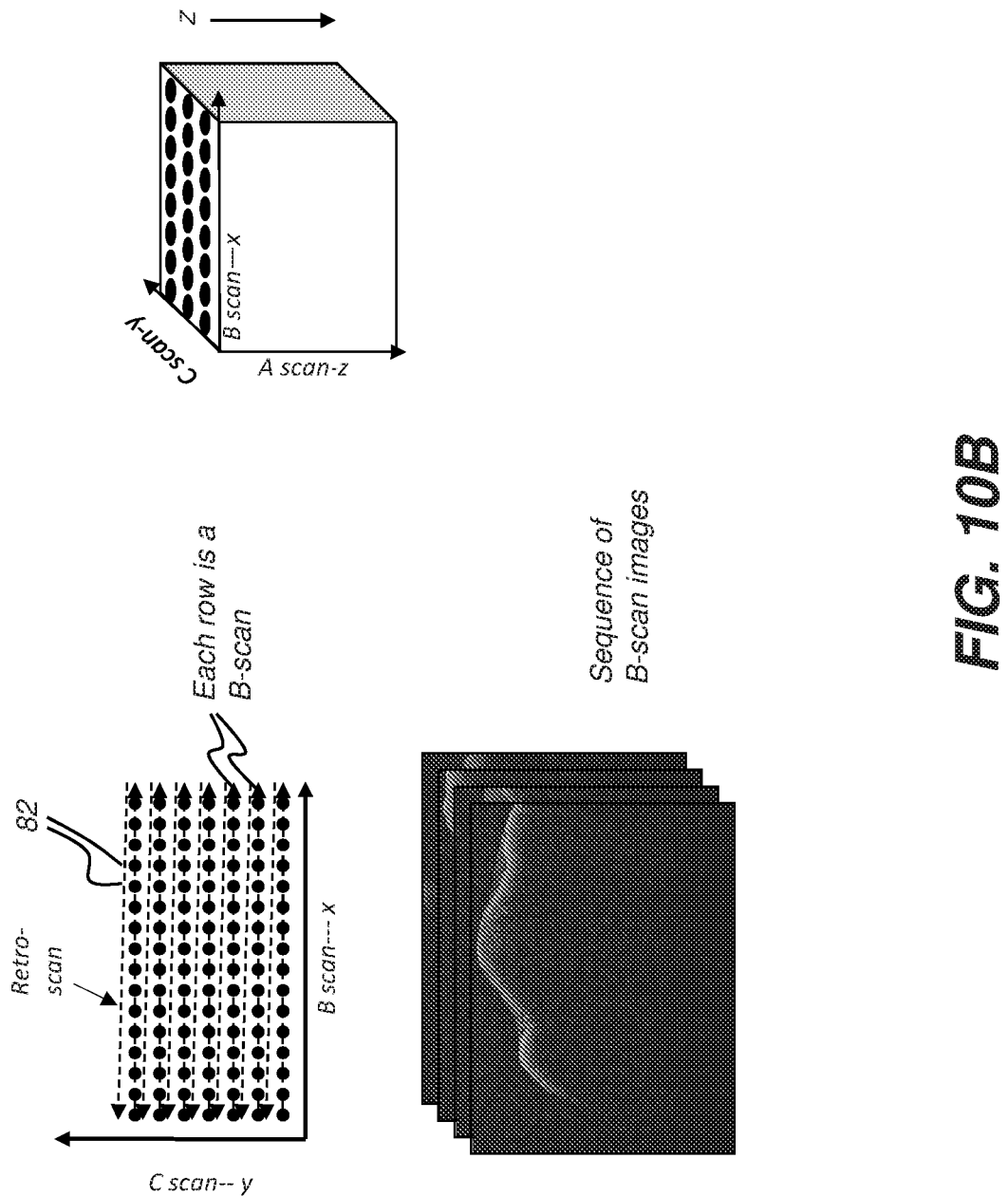
FIG. 10B shows an OCT scanning pattern for C-scan acquisition.

The schematic diagrams of FIGS. 10A and 10B show a scan sequence that can be used for forming tomographic images using the OCT apparatus of the present disclosure. The sequence shown in FIG. 10A shows how a single B-scan image is generated. A raster scanner 90 (FIG. 9) scans the selected light sequence over sample S, point by point. A periodic drive signal 92 as shown in FIG. 10A is used to drive the raster scanner 90 galvo mirrors to control a lateral scan or B-scan that extends across each row of the sample, shown as discrete points 82 extending in the horizontal direction in FIGS. 10A and 10B. At each of a plurality of points 82 along a line or row of the B-scan, an A-scan or depth scan, acquiring data in the z-axis direction, is generated using successive portions of the selected wavelength band. FIG. 10A shows drive signal 92 for generating a straightforward ascending sequence using raster scanner 90, with corresponding micro-mirror actuations, or other spatial light modulator pixel-by-pixel actuation, through the wavelength band. The retro-scan signal 93, part of drive signal 92, simply restores the scan mirror back to its starting position for the next line; no data is obtained during retro-scan signal 93.

It should be noted that the B-scan drive signal 92 drives the galvo mirror 94 for raster scanner 90 as shown in FIG. 9. At each incremental position, point 82 along the row of the B-scan, an A-scan is obtained. To acquire the A-scan data, tuned laser 50 or other programmable light source sweeps through the spectral sequence that is controlled by programmable filter 10 (FIGS. 1, 2A, 4, 5). Thus, in an embodiment in which programmable filter 10 causes the light source to sweep through a 30 nm range of wavelengths, this sequence is carried out at each point 82 along the B-scan path. As FIG. 10A shows, the set of A-scan acquisitions executes at each point 82, that is, at each position of the scanning galvo mirror 94. By way of example, where a DLP micro-mirror device is used as spatial light modulator 80, there can be 2048 measurements for generating the A-scan at each position 82.

FIG. 10A schematically shows the information acquired during each A-scan. An interference signal 88, shown with DC signal content removed, is acquired over the time interval for each point 82, wherein the signal is a function of the time interval required for the sweep, with the signal that is acquired indicative of the spectral interference fringes generated by combining the light from reference and feedback arms of the interferometer (FIGS. 6A, 6B). The Fourier transform generates a transform T for each A-scan. One transform signal corresponding to an A-scan is shown by way of example in FIG. 10A.

From the above description, it can be appreciated that a significant amount of data is acquired over a single B-scan sequence. In order to process this data efficiently, a Fast-Fourier Transform (FFT) is used, transforming the time-based signal data to corresponding frequency-based data from which image content can more readily be generated.

In Fourier domain OCT, the A scan corresponds to one line of spectrum acquisition which generates a line of depth (z-axis) resolved OCT signal. The B scan data generates a 2-D OCT image along the corresponding scanned line.

Raster scanning is used to obtain multiple B-scan data by incrementing the raster scanner 90 acquisition in the C-scan direction. This is represented schematically in FIG. 10B, which shows how 3-D volume information is generated using the A-, B-, and C-scan data.

As noted previously, the wavelength or frequency sweep sequence that is used at each A-scan point 82 can be modified from the ascending or descending wavelength sequence that is typically used. Arbitrary wavelength sequencing can alternately be used. In the case of arbitrary wavelength selection, which may be useful for some particular implementations of OCT, only a portion of the available wavelengths are provided as a result of each sweep. In arbitrary wavelength sequencing, each wavelength can be randomly selected, in arbitrary sequential order, to be used in the OCT system during a single sweep.

Figure 11:
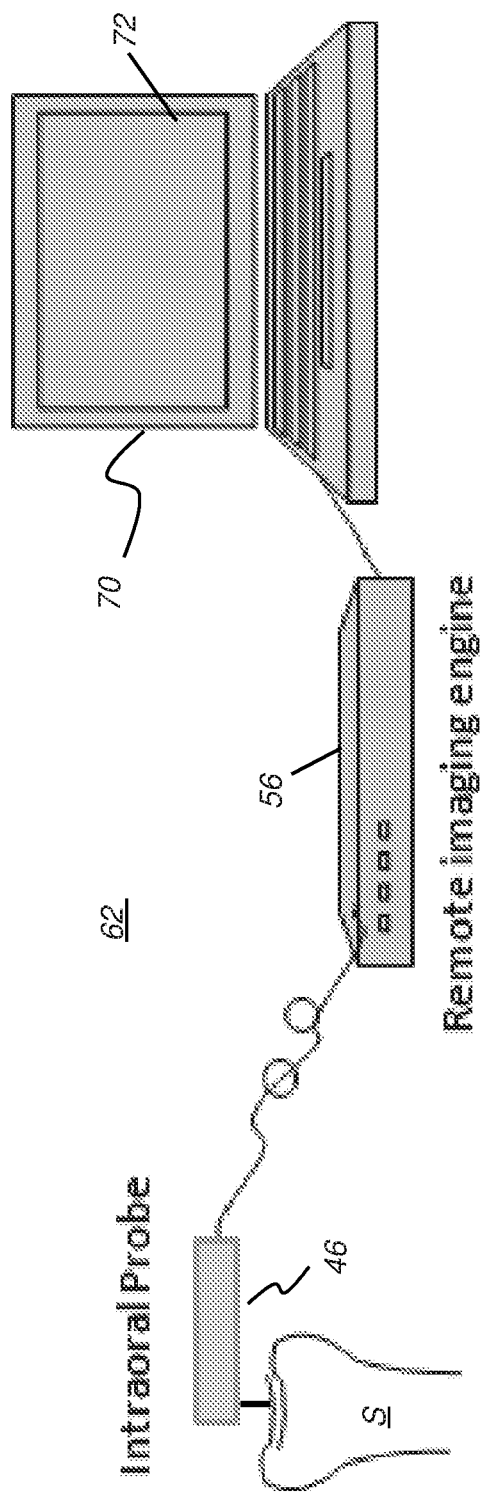
FIG. 11 is a schematic diagram that shows components of an intraoral OCT imaging system.

The schematic diagram of FIG. 11 shows probe 46 and support components for forming an intraoral OCT imaging system 62. An imaging engine 56 includes the light source, fiber coupler, reference arm, and OCT detector components described with reference to FIGS. 6A-7. Probe 46, in one embodiment, includes the raster scanner 90 or sample arm, but may optionally also contain other elements not provided by imaging engine 56. CPU 70 includes control logic and display 72.

The preceding description gives detailed description of OCT imaging system 62 using a DLP micro-mirror array 30 as one useful type of spatial light modulator that can be used for selecting a wavelength band from programmable filter 10. However, it should be noted that other types of spatial light modulator 80 could be used to reflect light of a selected wavelength band. A reflective liquid crystal device could alternately be used in place of DLP micro-mirror array 30, for example. Other types of MEMS (micro-electromechanical system devices) micro-mirror array that are not DLP devices could alternately be used.

Processing for OCT Imaging

Figure 12:
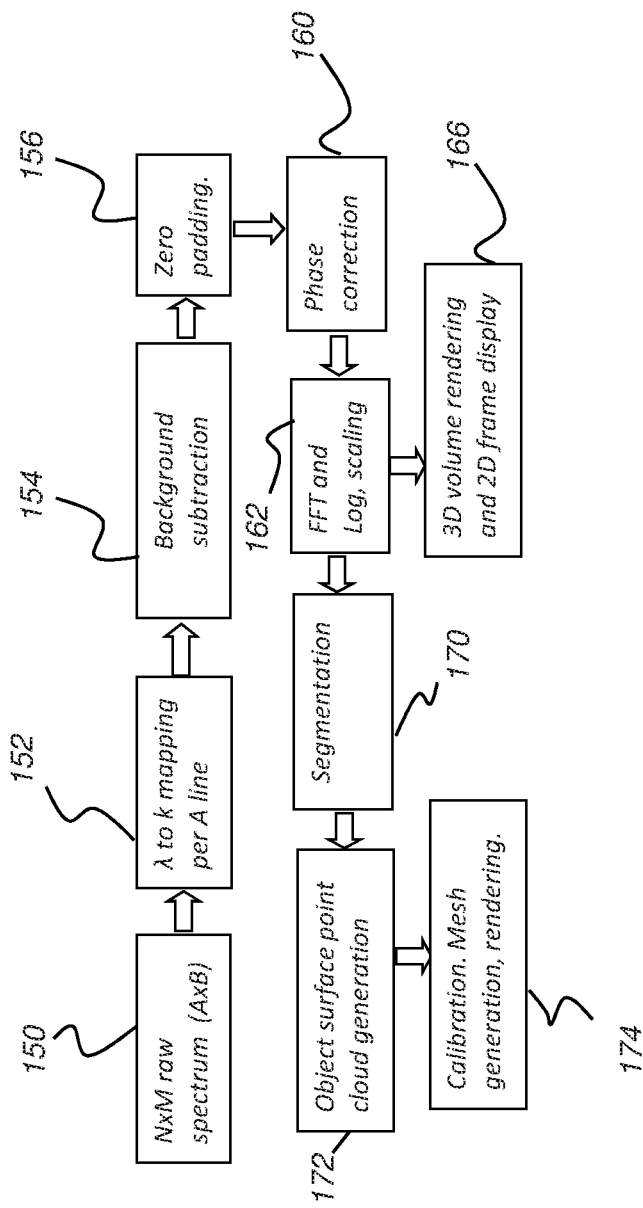
FIG. 12 is a process flow diagram that shows a sequence for OCT processing according to an embodiment of the present disclosure.

The logic flow diagram of FIG. 12 shows a sequence for OCT processing to obtain OCT imaging content along with a surface point cloud extracted from the OCT content according to an embodiment of the present disclosure. The raw 2-D spectral data 150 with numerous A scans per each B scan is provided over a linear wavelength λ, provided as M lines with N pixels per line. A mapping 152 then provides a wave-number value k for each corresponding wavelength λ. A background subtraction 154 executes, calculated along the B direction for each k value, and a line of background signal is obtained. Background subtraction 154, performed on each A line, helps to remove fixed pattern noise. In a zero padding operation 156 and a phase correction process 160 spectrum sampling is corrected and dispersion-induced OCT signal broadening obtained. An FFT processing step 162 provides processing and scaling of the phase-corrected data to provide input for a 3-D volume rendering and 2-D frame display rendering 166, useful for visualization and diagnostic support. At the conclusion of step 162, the OCT image content is available.

Subsequent processing in the FIG. 12 sequence then extracts the point cloud for surface characterization. A segmentation step 170 is then executed to extract the surface contour data from the OCT volume data. Object surface point cloud generation step 172 provides the surface point clouds of the measured object. Point clouds can then be calibrated and used for mesh rendering step 174 along with further processing. Geometric distortion calibration of OCT images can be executed in order to help correct shape distortion. Unless properly corrected, distortion can result from the scanning pattern or from the optical arrangement that is used. Distortion processing can use spatial calibration data obtained by using a calibration target of a given geometry. Scanning of the target and obtaining the scanned data establishes a basis for adjusting the registration of scanned data to 3-D space, compensating for errors in scanning accuracy. The calibration target can be a 2-D target, imaged at one or more positions, or a 3-D target.

Segmentation step 170, object surface point cloud generation step 172, and mesh generation and rendering step 174 of the FIG. 12 sequence obtain surface contour data from OCT volume measurements. Importantly, results of these steps are the reconstructed surfaces of the object measured by OCT. This extracted OCT surface imaging content can be directly merged with results measured by a surface contour imaging device that shares the same coordinate system as the OCT content, using coordinate matching methods commonly known in the art, such as iterative closest point (ICP) merging. OCT and surface contour image data content can thus be automatically registered, either as point clouds or mesh, by ICP merging, without requiring additional steps.

The extracted OCT surface data, by itself or in registration with surface contour image data, can be displayed, stored, or transmitted to another computer or storage device.

Depending on applications and imaging conditions, various image segmentation algorithms can be used in segmentation step 170 to extract object surfaces. Image segmentation algorithms such as simple direct threshold, active contour level set, watershed, supervised and unsupervised image segmentation, neural network based image segmentation, spectral embedding and max-flow/min-cut graph based image segmentation, etc. are well known in the image processing fields and can be utilized; they can be applied to the entire 3-D volume or separately to each 2-D frame of the OCT data.

Figure 13B:
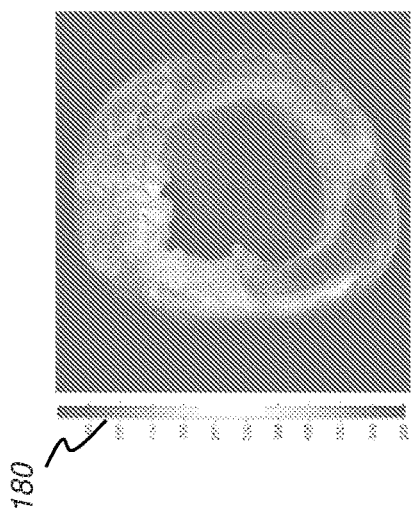
FIGS. 13A-13E show different types of imaging content acquired and generated as part of the OCT processing sequence, using the example of a tooth image having a severe cavity.
Figure 13E:
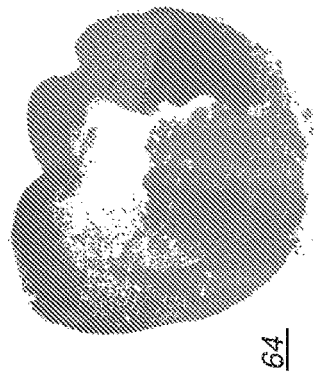
Figure 13A:
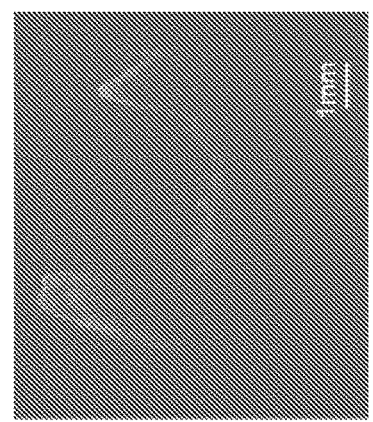
Figure 13D:
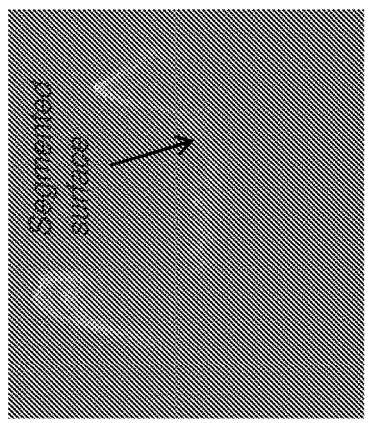
Figure 13C:
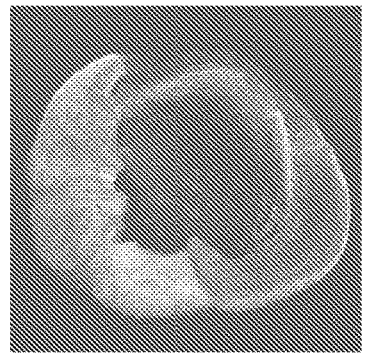

FIGS. 13A-13E show different types of imaging content acquired and generated as part of the OCT processing sequence, using the example of a tooth image having a severe cavity. FIG. 13A shows a 2-D slice that corresponds to a B-scan for OCT imaging. FIG. 13B shows a depth-encoded color projection of the tooth, with an optional color bar 180 as a reference. FIG. 13C shows a corresponding slice of the volume rendering obtained from the OCT imaging content. FIG. 13D shows the results of segmentation processing of FIG. 13A in which points along the tooth surface are extracted. FIG. 13E shows a surface point cloud 64 of the tooth generated from the OCT volume data. The surface point cloud 64 can be obtained from the OCT volume data following segmentation, as shown previously with respect to the sequence of FIG. 12.

Surface Contour Imaging

Unlike OCT imaging described previously, surface contour imaging uses reflectance imaging and provides data for characterizing a surface, such as surface structure, curvature, and contour characteristics, but does not provide information on material that lies below the surface. Contour imaging data or surface contour image data can be obtained from a structured light imaging apparatus or from an imaging apparatus that obtains structure information related to a surface from a sequence of 2-D reflectance images obtained using visible light illumination, generally in the range above about 380 and less than a 740 nm threshold, near-infrared light near and extending higher than 740 nm, or ultraviolet light wavelengths below 380 nm. Alternate techniques for contour imaging include structured light imaging as well as other known techniques for characterizing surface structure using reflectance imaging techniques, such as feature tracking by triangulation, structure-from-motion photogrammetry, time-of-flight imaging, and depth-from-focus imaging, for example. Contour image content can alternately be extracted from volume image content, such as from the OCT volume content, as described previously with respect to FIG. 12, by identifying and collecting only those voxels that represent surface tissue, for example.

The phrase "patterned light" is used to indicate light that has a predetermined spatial pattern, such that the light has one or more features such as one or more discernable parallel lines, curves, a grid or checkerboard pattern, or other features having areas of light separated by areas without illumination. In the context of the present disclosure, the phrases "patterned light" and "structured light" are considered to be equivalent, both used to identify the light that is projected onto the subject in order to derive contour image data.

In structured light imaging, a pattern of lines, or other structured pattern, is projected from the imaging apparatus toward the surface of an object from a given angle. The projected pattern from the surface is then viewed from another angle as a contour image, taking advantage of triangulation in order to analyze surface information based on the appearance of contour lines. Phase shifting, in which the projected pattern is incrementally shifted spatially for obtaining additional measurements at the new locations, is typically applied as part of structured light imaging, used in order to complete the contour mapping of the surface and to increase overall resolution in the contour image.

Figure 14:
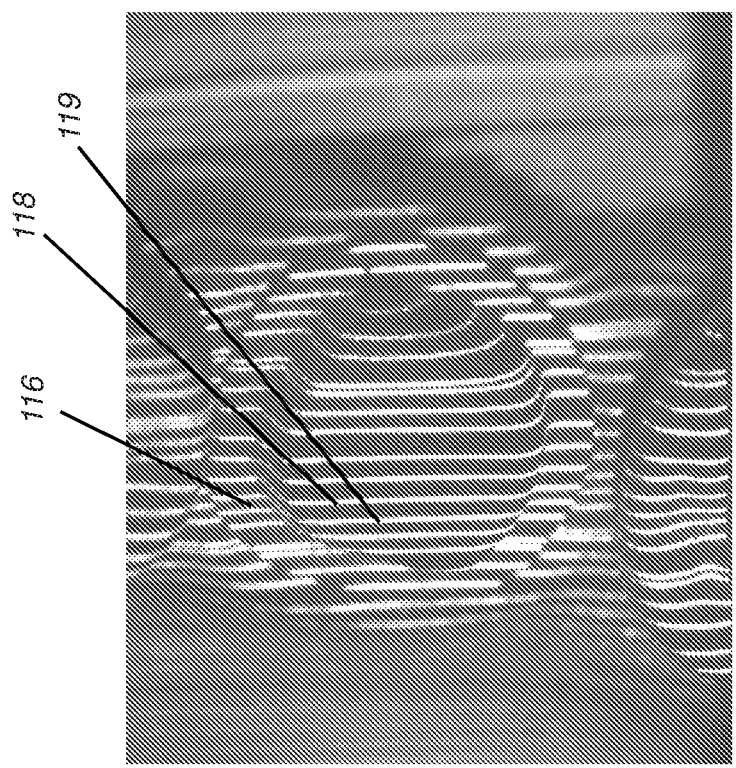
FIG. 14 is a perspective view that shows a pattern of light projected onto a contoured surface.

FIG. 14 shows surface imaging using a pattern with multiple lines of light. Incremental shifting of the line pattern and other techniques help to compensate for inaccuracies and confusion that can result from abrupt transitions along the surface, whereby it can be difficult to positively identify the segments that correspond to each projected line. In FIG. 14, for example, it can be difficult over portions of the surface to determine whether line segment 116 is from the same line of illumination as line segment 118 or adjacent line segment 119.

By knowing the instantaneous position of the scanner and the instantaneous position of the line of light within an object-relative coordinate system when the image was acquired, a computer equipped with appropriate software can use triangulation methods to compute the coordinates of numerous illuminated surface points. As a result of this image acquisition, a point cloud of vertex points or vertices can be identified and used to characterize the surface contour. The points or vertices in the point cloud then represent actual, measured points on the three dimensional surface of an object.

The pattern can be imparted to the patterned light using a spatial light modulator, such as a Digital Light Processor (DLP) or using a diffraction grating, for example. The pattern can also be generated as a raster pattern by actuated deflection of light emission coordinated with the scanner hardware, such as by the use of a microelectrical-mechanical system (MEMS) or a galvo.

It should be noted that reflectance imaging can be used for purposes other than surface contour imaging. Reflectance images of the tooth surface, for example, can be used for determining color, surface texture, and other visible characteristics of the tooth surface.

Combining OCT with Surface Contour and other Reflectance Imaging

Certain exemplary method and/or apparatus embodiments can provide combined OCT and structured light imaging for dental imaging. An embodiment of the present disclosure, shown in the simplified schematic diagram of FIG. 15 as an imaging apparatus 200, provides an exemplary mechanism and methods that combine OCT and structured light imaging in a single imaging apparatus for generating both depth-resolved tomography image content and a surface contour image content that can be readily registered to each other and acquired either simultaneously or nearly simultaneously, that is, acquired in a single imaging operation rather than requiring separate scanning passes by the operator. Significantly, the imaging paths for OCT and surface contour imaging are spectrally separated, so that the wavelengths used in each imaging path are distinct from each other. The light for OCT illumination imaging lies above a threshold wavelength and the light for surface contour imaging below the threshold wavelength.

Figure 15:
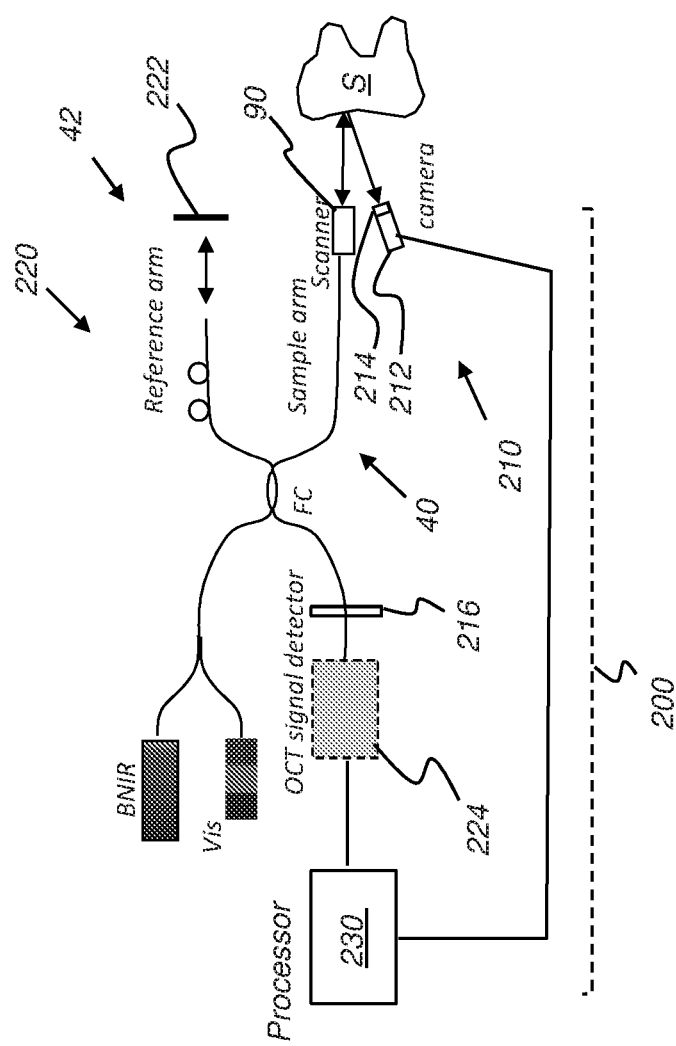
FIG. 15 is a schematic diagram showing components of an imaging apparatus for combined OCT and surface contour imaging.

The simplified schematic diagram of FIG. 15 shows two imaging subsystems, a reflectance imaging or surface contour imaging system 210 and an OCT imaging system 220, that cooperate as part of imaging apparatus 200. Surface contour imaging system 210 uses visible light Vis illumination that is conveyed to a sample S, such as a tooth. According to an embodiment of the present disclosure, the Vis light wavelength range that is used extends from about 380 nm to about 740 nm and is detected by a camera 212.

The OCT imaging system 220 in FIG. 15 uses BNIR light from a broadband coherent near-infrared light source used for OCT imaging with wavelength ranging from 740 nm to 1550 nm. A fiber coupler FC splits the BNIR light into reference arm 42 and sample arm 40. Light in reference arm 42 is retro-reflected by a reference mirror 222 and coupled to fiber coupler FC as reference light for interferometry, as described previously with reference to schematic diagrams of FIGS. 6A and 6B. Light in sample arm 40 is conveyed to sample S such as a tooth via raster scanner 90 as shown schematically in FIG. 9 and supporting focusing optical components, not shown. A portion of the BNIR light that is backscattered by the sample S is collected by the same optics of sample arm 40 and coupled back to sample arm 40. The reference light and sample light interfere at fiber coupler FC.

The light paths for surface contour imaging system 210 and OCT imaging system 220 in FIG. 15 enter fiber coupler FC on the same path but are spectrally isolated from each other, above and below the threshold value, as noted previously. Optionally, to provide additional isolation of the two systems, spectral filters can be employed. Spectral filter 216, placed in between fiber coupler FC and OCT signal detector 224, ensures that only the broad band NIR interference light is detected by OCT signal detector 224. Camera 212 senses only visible light, and BNIR light is blocked by a different spectral filter 214. The reflected visible light pattern is captured by camera 212 at an appropriate angle with respect to the patterned Vis illumination direction. For surface contour imaging, a predetermined illumination pattern impinges onto sample S with modulation of visible light intensity, under control of raster scanner 90.

Conveniently, the same raster scanner 90 and associated optics convey both the BNIR light for OCT and Vis patterned illumination for surface contour imaging to sample S. Because OCT and surface contour imaging share the same raster scanner 90, when system calibration is done on imaging apparatus 200, both OCT and surface contour imaging are automatically calibrated to the same coordinate system. A processor 230, in signal communication with both OCT signal detector 224 and related components and with camera 212, controls and coordinates the behavior of both surface contour imaging system 210 and OCT imaging system 220 for acquisition of both OCT and surface contour image content.

Figure 16A:
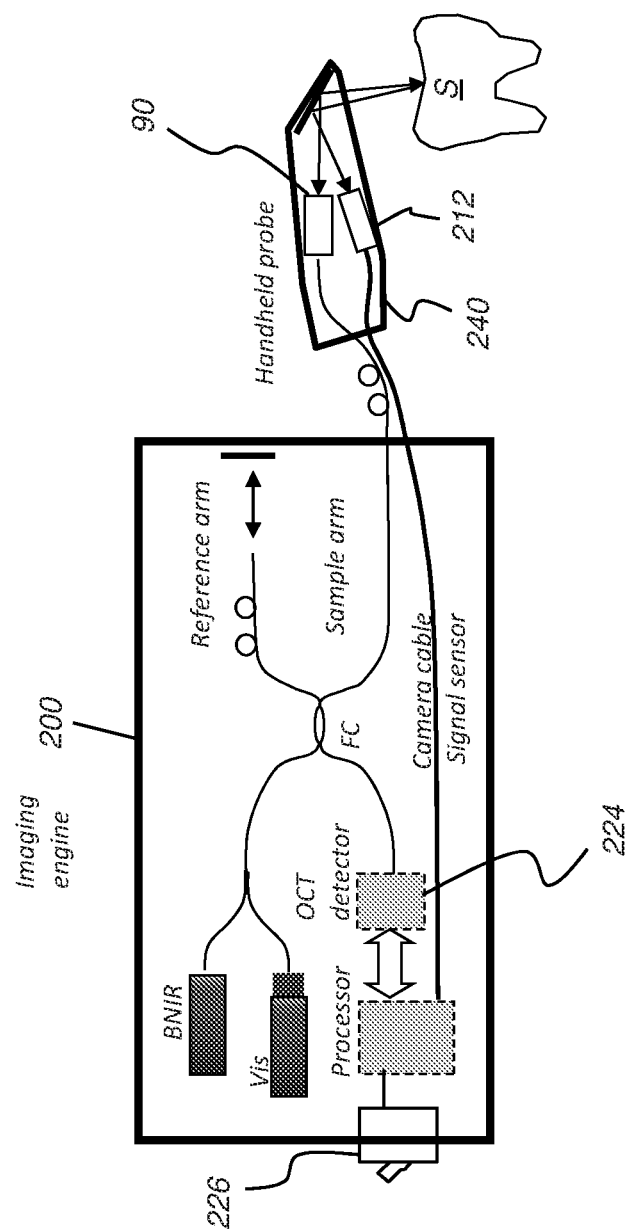
FIG. 16A is a schematic diagram showing an imaging apparatus having a handheld probe for combined OCT and surface contour imaging.

The schematic diagram of FIG. 16A shows an embodiment of imaging apparatus 200 that combines raster scanner 90 and camera 212 optics as parts of a handheld probe 240 for intraoral imaging, wherein sample S is an intraoral feature such as a tooth, gum tissue or other supporting structure. Components of probe 240 can alternately include additional portions of the OCT imaging and reflective imaging components. Probe 240 connects to processor 230 by means of wired connection, such as for signal connection and electrical power, and provides optical signals over an optical fiber cable connection.

Imaging apparatus 200 can work in either OCT depth imaging or surface contour imaging mode, operating in either mode separately, or capturing image content in both modes simultaneously. In addition, the visible light source Vis and camera 212 can be used for preview only in support of OCT imaging. FIG. 16A also shows a mode switch 226 that can be used for selection of operating mode, such as one of reflectance imaging, OCT imaging, or both imaging types. Alternately, mode switch 226 can reside on handheld probe 240 or can be a "soft" switch, toggled by operator instruction entry on the user interface of processor 230.

In one exemplary embodiment, OCT depth imaging can be retrofit to a surface contour imaging apparatus.

Figure 16B:
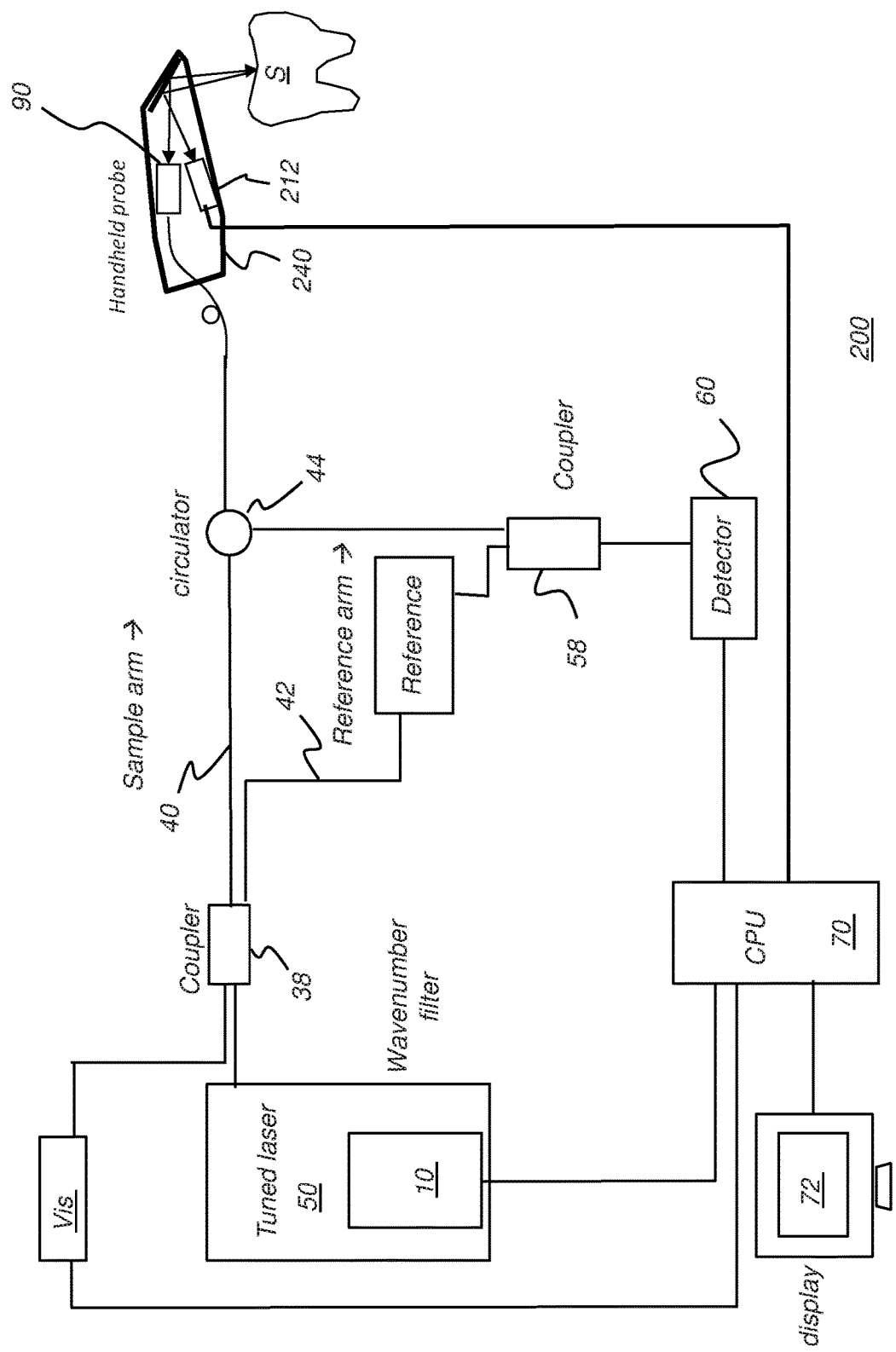
FIG. 16B is a schematic diagram showing an imaging apparatus that combines surface contour and OCT imaging.

FIG. 16B is a schematic diagram showing an imaging apparatus that combines surface contour and OCT imaging and shows a visible light source providing the visible light Vis through coupler 38 and circulator 44 for surface contour imaging. The visible light can share the same optical path used for providing sample light in the OCT imaging subsystem in probe 240. This allows simultaneous or near-simultaneous OCT and reflectance image capture, with the light from the OCT and visible light Vis traveling along the same path. It should be noted that the OCT scan typically obtains only a few complete frames per second, whereas the reflectance imaging used for surface contour characterization or for color characterization of a tooth or other surface can capture and process images at a much faster rate.

FIG. 16B shows the OCT imaging system with a Mach-Zehnder interferometer configuration and a swept-source OCT implementation only by way of illustration. Alternative type of interferometer configurations, such as Michelson interferometer, can also be used. An alternative type of OCT implementation, such as spectral-domain OCT or time-domain OCT, can also be used.

Figure 17A:
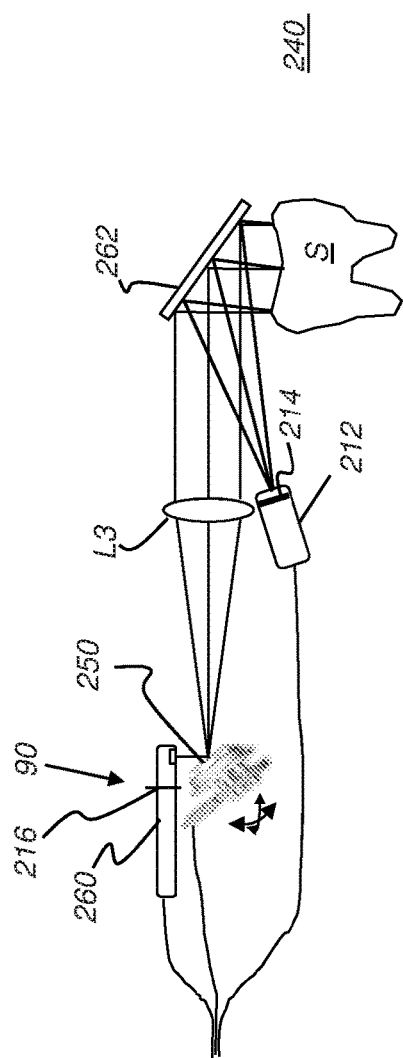
FIG. 17A is a schematic view that shows a probe configuration using a single two-axis scanning mirror.

There are a number of arrangements that can be used for probe 240 components. FIG. 17A shows a configuration using a single two-axis scanning mirror 250 as raster scanner 90. Single two-axis scanning mirror 250 can be a 2-axis MEMS mirror, for example. Optical components in an optical module 260 provide collimated light to scanning mirror 250. Light from scanning mirror 250 is directed through an objective lens L3 that focuses the collimated beam. An optional folding mirror 262 folds the light path to direct the focal region to sample S and to direct reflected light to camera 212, which includes an imaging lens and a sensor (not shown separately). Light for both OCT and surface contour (reflectance) imaging is emitted from optical module 260. This simplifies calibration that registers the OCT imaging to the contour surface imaging, or other reflectance imaging such as imaging for characterizing tooth color. Because the scanning mirror 250 position is controlled by processing logic, this position is known at each instant, whether the emitted light is BNIR light used for OCT imaging or Vis light used for reflectance imaging. Calibration of the scanning hardware serves both OCT and reflectance imaging paths.

As shown schematically in FIG. 17A, an optional filter 214 can be used with camera 212 to further distinguish the OCT from the surface contour imaging path, rejecting OCT wavelengths and other unwanted light. A filter 216 can be provided as part of optical module 260, for blocking Vis light from reaching the OCT detector.

Figure 17B:
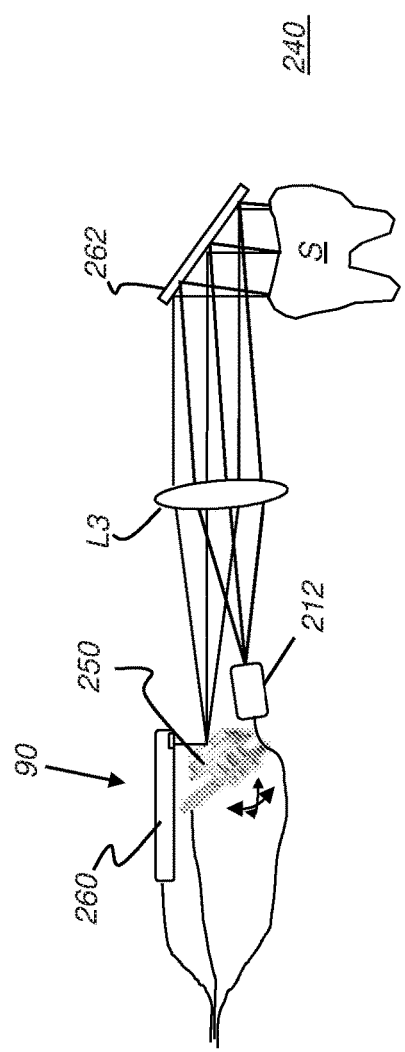
FIG. 17B is a schematic view that shows an alternative probe configuration using a single two-axis scanning mirror and a lens that is shared by both projection and imaging light paths.

The schematic view of FIG. 17B shows a configuration that also uses two-axis scanning mirror 250 as raster scanner 90. Optical components in optical module 260 provide collimated light for both OCT and visible light systems to scanning mirror 250. Light from scanning mirror 250 is directed through objective lens L3 that focuses the collimated beam. Folding mirror 262 folds the light path to direct the light to sample S and form the focal region at camera 212. Lens L3 also forms part of the imaging path in the FIG. 17B arrangement, directing light to camera 212.

Figure 17C:
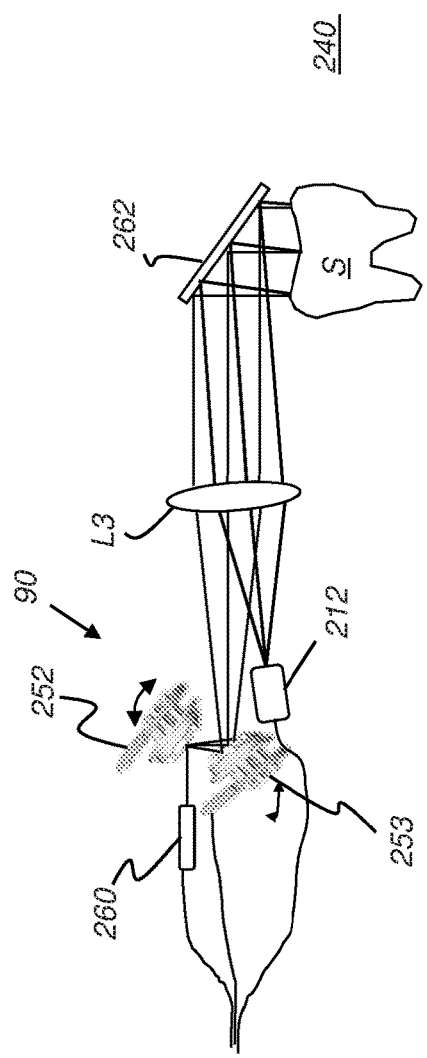
FIG. 17C is a schematic view that shows a probe configuration using a two-mirror, two-axis scanner.

FIG. 17C is a schematic view that shows a probe 240 configuration using a two-mirror 252, 253, two-axis raster scanner 90. Each mirror 252, 253 is a single-axis mirror; it can be a galvo mirror or a single-axis MEMS mirror, for example. Optical module 260 directs collimated light to mirror 252, which scans about a first axis. The reflected light is directed to mirror 253 that scans about a second axis and directs the light through objective lens L3. Folding mirror 262 folds the light path to direct the focal region to sample S and to direct reflected Vis light to camera 212. Lens L3 also forms part of the imaging path in the FIG. 17C arrangement, directing light to camera 212.

Figure 17D:
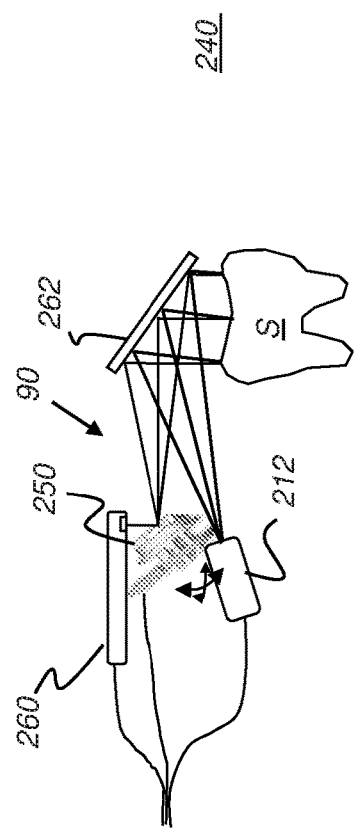
FIG. 17D is a schematic view that shows a probe configuration using a single two-axis scanning mirror without separate focusing optics.

FIG. 17D is a schematic view wherein optical module 260 generates focused light, so that an external lens is not needed. Two-axis scanning mirror 250 directs this light to the sample S and directs image-bearing light to camera 212.

Figure 17E:
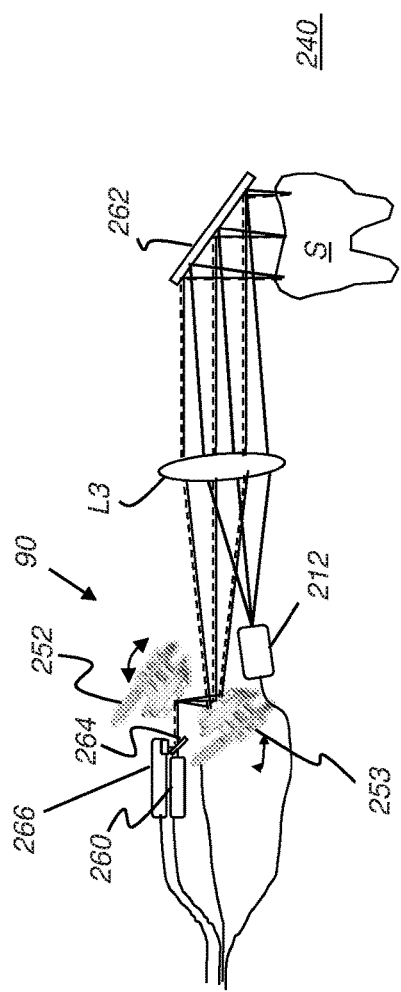
FIG. 17E is a schematic view that shows a probe configuration combining OCT scanning with external line sweeping.
Figure 17F:
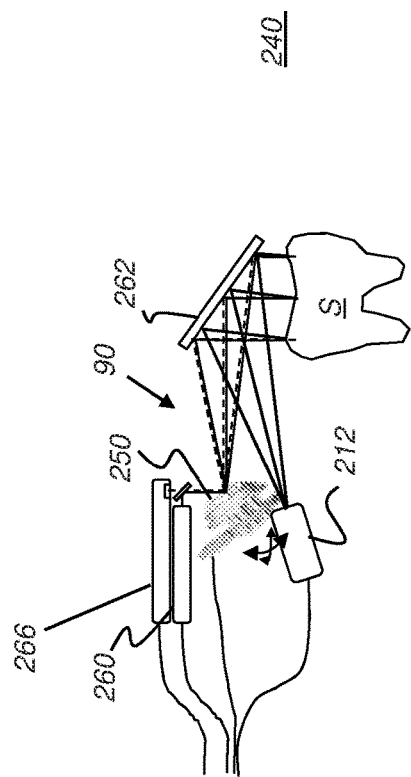
FIG. 17F is a schematic view that shows the second configuration combining OCT scanning with external line sweeping.

FIGS. 17E and 17F are schematic diagrams showing alternate scanning arrangements in which another optical module 266 is used to provide Vis light. In this scanning arrangement, visible light Vis takes a separate path to the handheld probe, unlike the arrangement shown in the diagram of FIG. 16B. Beamsplitter 264 combines Vis light from optical module 266 and BNIR light from optical module 260 so that the two lights follow the same path from beamsplitter 264 to sample S. In FIG. 17E, the generated line is scanned toward sample S by single-axis mirrors 252, 253. FIG. 17F shows an alternate embodiment using a single two-axis mirror 250 to shift line position for surface contour imaging.

As another option for surface contour characterization, surface segmentation can also be used to extract a point cloud representative of a real surface from OCT images of an object. The extracted geometric shape of the point cloud matches that obtained with structured light imaging method.

As noted previously, both the OCT and reflectance image content can be acquired with reference to the same raster scanner coordinates. Point clouds generated from both systems also share the same coordinates. Once surface data is extracted from the OCT volume image by segmentation, registration of the surface data from OCT to the contour surface imaging output is simplified.

Light Source Options

Visible light Vis can be of multiple wavelengths in the visible light range. The Vis source can be used for color-coding of the projected structured light pattern, for example. The Vis source can alternately be used for white light image preview or for tooth shade measurement or color or texture characterization.

Vis light can be provided from a conventional bulb source or may originate in a solid-state emissive device, such as a laser or one or more light-emitting diodes (LEDs). Individual Red, Green, and Blue LEDs are used to provide the primary color wavelengths for reflectance imaging.

In addition to providing a structured light pattern, the Vis source can alternately provide light of particular wavelengths or broadband light that is scanned over the subject for conventional reflectance imaging, such as for detecting tooth shade, for example, or for obtaining surface contour data by a method that does not employ a light pattern, such as structure-from-motion imaging, for example.

A violet light, in the near-UV region can be used as the excitation light for tooth fluorescence imaging. Backscattered fluorescence can be collected by the OCT light path. The fluorescence image can be detected by the same detector path of the Fourier domain OCT, but at a different lateral spectrum location.

Figure 18:
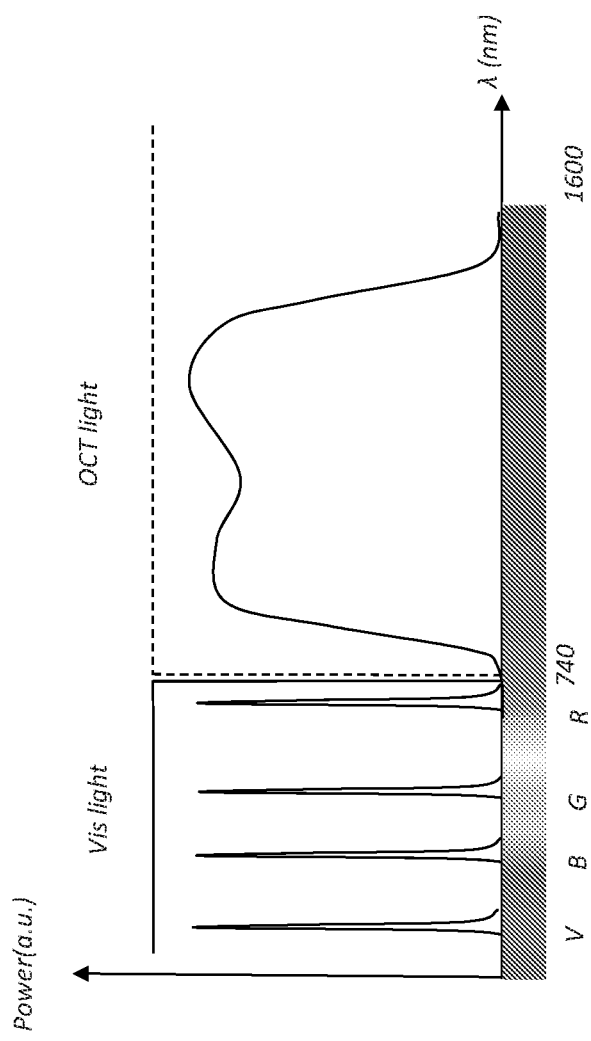
FIG. 18 shows a light source selection guide for the different types of imaging provided from the apparatus of the present disclosure.

FIG. 18 shows exemplary spectral values for light sources. In general, violet V wavelengths in the near UV region, below about 380 nm, are typically favored for fluorescence imaging. The visible light Vis, with components labeled B, G, R for primary Blue, Green, and Red colors ranging from above 380 to below 740 nm, is usually selected for structured light pattern projection. Infrared light above 740 nm is usually selected for OCT imaging.

An embodiment of the present disclosure provides an active triangulation system for contour imaging that includes an illumination path that is shared by both an OCT system and a reflectance imaging system. Camera 212 in the imaging path (FIGS. 17A-17F) views the sample at an oblique angle with respect to the illumination path. The visible light source used for generating the structured light pattern emits light at different wavelengths not used for the OCT system, so that the two optical systems can operate without perceptible crosstalk or interference between them. The visible light can encode a predetermined light pattern for structured light imaging by appropriately controlling the timing of the visible light source with respect to motion of raster scanner 90. Distorted light patterns from the subject surface are imaged by the optical system in the imaging path and captured by the camera. Decoding the light pattern generates the surface contour of the imaged object.

Consistent with an embodiment of the present invention, a computer program utilizes stored instructions that perform on image data that is accessed from an electronic memory. As can be appreciated by those skilled in the image processing arts, a computer program for operating the imaging system in an embodiment of the present disclosure can be utilized by a suitable, general-purpose computer system operating as CPU 70 as described herein, such as a personal computer or workstation. However, many other types of computer systems can be used to execute the computer program of the present invention, including an arrangement of networked processors, for example. The computer program for performing the method of the present invention may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. The computer program for performing the method of the present disclosure may also be stored on computer readable storage medium that is connected to the image processor by way of the internet or other network or communication medium. Those skilled in the art will further readily recognize that the equivalent of such a computer program product may also be constructed in hardware.

It should be noted that the term "memory", equivalent to "computer-accessible memory" in the context of the present disclosure, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer is also considered to be a type of memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It will be understood that the computer program product of the present disclosure may make use of various image manipulation algorithms and processes that are well known. It will be further understood that the computer program product embodiment of the present disclosure may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present disclosure, are not specifically shown or described herein and may be selected from such algorithms, systems, hardware, components and elements known in the art.

Certain exemplary method and/or apparatus embodiments according to the application can provide virtual definition of the base of a dental virtual model. Exemplary embodiments according to the application can include various features described herein (individually or in combination).

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations/embodiments, such feature can be combined with one or more other features of the other implementations/embodiments as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by at least the following claims.

The invention claimed is:

1. An optical apparatus for imaging a sample, the apparatus comprising:
    an optical coherence tomography imaging apparatus having:
        a) a first light source that generates low coherence light of wavelengths above a threshold wavelength;
        b) a signal detector that obtains an interference signal between a first portion of the low coherence light scattered from the sample and a second portion of the low coherence light reflected from a reference;
    a surface contour imaging apparatus having:
        a) a second light source that emits one or more wavelengths of surface illumination below the threshold wavelength;
        b) a camera disposed at an oblique angle with respect to the direction of the surface illumination incident at the sample to acquire images from the illumination reflected from the sample;
    a probe that has a raster scanner wherein the low coherence light and the surface illumination share the same path from the raster scanner to the sample; and
    a processor that is programmed with instructions that coordinate activation of the first and second light sources, actuation of the raster scanner, and acquisition of data from the signal detector and the camera and further programmed with instructions to display, store, or transfer images from the acquired data.

2. The apparatus of claim 1 wherein the threshold wavelength is about 740 nm.

3. The apparatus of claim 1 wherein the first and second light sources follow the same path to the probe.

4. The apparatus of claim 1 wherein the first and second light sources follow different paths to the probe.

5. The apparatus of claim 1 wherein the raster scanner comprises a mirror that is actuable in one or two axes.

6. The apparatus of claim 1 wherein the raster scanner comprises at least one scanner mirror that is a MEMS device or a galvo device.

7. The apparatus of claim 6 wherein the at least one scanner mirror, in cooperation with the second light source, imparts a structured light pattern to the sample.

8. The apparatus of claim 1 wherein the raster scanner comprises two separate actuable scanner mirrors.

9. The apparatus of claim 1 wherein the sample is an intraoral feature.

10. The apparatus of claim 1 further comprising at least one objective lens that is disposed to focus light from either or both of the first and second light source onto the sample.

11. The apparatus of claim 1 further comprising an optical filter for blocking light of the second light source from the signal detector.

12. The apparatus of claim 1 further comprising an optical filter for blocking light of the first light source from the camera.

13. The apparatus of claim 1 wherein the second light source is an LED.

14. The apparatus of claim 1 wherein the first light source is a superluminescent LED, a swept source, short pulse laser, or a supercontinuum light source.

15. The apparatus of claim 1 wherein the signal detector is a spectrometer or photodetector.

16. The apparatus of claim 1 wherein the optical coherence tomography imaging apparatus and surface contour imaging apparatus acquire data simultaneously or near-simultaneously in a single imaging operation.

17. The apparatus of claim 1 wherein the interference signal is obtained from a Michelson or Mach-Zehnder interferometer.

18. The apparatus of claim 1 wherein the optical coherence tomography imaging apparatus is retrofit to the probe including the surface contour imaging apparatus.

19. The apparatus of claim 1 wherein the processor is further programmed with instructions to:
    generate volume data of the sample according to the obtained interference signal;
    segment the generated volume data to extract surface data to construct an OCT 3D surface contour of the sample;
    generate surface contour data using the acquired images of the camera of the surface contour imaging apparatus; and
    register the OCT 3D surface contour of the sample to the generated surface contour data of the surface contour imaging apparatus.

20. The apparatus of claim 1 wherein a single light source provides the low coherence light of wavelengths above the threshold wavelength and the one or more wavelengths of surface illumination below the threshold wavelength.

21. A method for imaging a sample comprising:
    a) obtaining optical coherence tomography imaging content with steps of:
        (i) generating low coherence light of wavelengths above a threshold wavelength;
        (ii) obtaining an interference signal between a first portion of the low coherence light scattered from the sample and a second portion of the low coherence light reflected from a reference;
b) obtaining surface contour imaging content with steps of:
(i) emitting one or more wavelengths of illumination light below the threshold wavelength;
(ii) acquiring images of the sample from an oblique angle with respect to the direction of the illumination light incident at the sample; and
c) directing the low coherence light and the illumination light through the same path to the sample by an actuable scanner mirror,
wherein optical coherence tomography imaging and surface contour imaging content are obtained in the same coordinate system in a single imaging operation.

22. The method of claim 21 further comprising coordinating activation of the low coherence light and the illumination light, the actuable scanner mirror, and acquisition of images.

23. The apparatus of claim 22 wherein activation of the actuable scanner mirror imparts a structured light pattern to the illumination light.

24. The method of claim 21 wherein optical coherence tomography imaging content and surface imaging content are obtained simultaneously or near simultaneously.

25. The method of claim 21 wherein the threshold wavelength is near 740 nm.

26. The method of claim 21 further comprising extracting a 3D point cloud of the sample's surface from the obtained optical coherence tomography images of the sample.

27. The method of claim 26 wherein extracting the 3D point cloud of the sample's surface is done using a segmentation algorithm.

28. A method for imaging a sample comprising:
obtaining optical coherence tomography imaging content, comprising:
a) generating low coherence light having wavelengths above a threshold wavelength using a first light source;
b) generating illumination light having one or more wavelengths below the threshold wavelength using a second light source;
c) obtaining an interference signal between a first portion of the low coherence light scattered from the sample and a second portion of the low coherence light reflected from a reference;
d) generating volume data of the sample according to the obtained interference signal;
e) segmenting the generated volume data to extract surface data to construct a first 3D surface contour of the sample; and
f) displaying, storing, or transmitting the constructed first 3D surface contour of the sample;
wherein the low coherence light from the first light source and the illumination light from the second light source share the same path from a raster scanner to the sample.

29. The method of claim 28 further comprising:
obtaining surface contour image content, comprising:
a) acquiring one or more images of the sample from an oblique angle with respect to the direction of the illumination light incident at the sample; and
b) generating a second 3D surface contour of the sample according to the acquired images;
wherein optical coherence tomography imaging content and surface contour image content are obtained in a single imaging operation in the same coordinate system.

30. The method of claim 29 further comprising registering the first 3D surface contour of the sample to the second 3D surface contour of the sample.

31. The method of claim 30 wherein registering step is done using an iterative closest point algorithm.

32. The method of claim 29 further comprising calibrating using a calibration target.

33. The method of claim 28 wherein the sample is an intraoral feature.

* * * * *